US008802680B2

(12) United States Patent
Prabhu et al.

(10) Patent No.: US 8,802,680 B2
(45) Date of Patent: Aug. 12, 2014

(54) COMPOSITIONS, METHODS AND KITS FOR TREATING LEUKEMIA

(75) Inventors: Kumble Sandeep Prabhu, State College, PA (US); Robert Frank Paulson, State College, PA (US); Shailaja Hegde, State College, PA (US); Naveen Kaushal, State College, PA (US); Ujjawal Hitendra Gandhi, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 13/538,297

(22) Filed: Jun. 29, 2012

(65) Prior Publication Data

US 2013/0005737 A1 Jan. 3, 2013

Related U.S. Application Data

(60) Provisional application No. 61/502,677, filed on Jun. 29, 2011, provisional application No. 61/535,149, filed on Sep. 15, 2011, provisional application No. 61/635,458, filed on Apr. 19, 2012.

(51) Int. Cl.
*A61K 31/19* (2006.01)
*A61K 31/506* (2006.01)

(52) U.S. Cl.
USPC .................... 514/252.18; 514/573; 514/530

(58) Field of Classification Search
CPC A61K 31/202; A61K 31/513; A61K 31/5575
USPC .................................. 514/252.18, 573, 530
See application file for complete search history.

(56) References Cited

U.S. PATENT DOCUMENTS

| | | | | |
|---|---|---|---|---|
| 5,605,922 | A * | 2/1997 | DeSantis et al. | 514/392 |
| 6,087,401 | A | 7/2000 | Koyama et al. | |
| 6,987,103 | B2 * | 1/2006 | Robin et al. | 514/214.01 |
| 7,183,440 | B2 | 2/2007 | Roberts et al. | |
| 2003/0144330 | A1 | 7/2003 | Spiegelman et al. | |
| 2005/0020687 | A1 | 1/2005 | Santoro et al. | |
| 2009/0054524 | A1 | 2/2009 | Karin et al. | |
| 2011/0105415 | A1 | 5/2011 | Khan | |

FOREIGN PATENT DOCUMENTS

| | | |
|---|---|---|
| EP | 175468 | 8/2007 |
| EP | 778269 | 9/2011 |
| JP | 2004010563 | 1/2004 |
| JP | 11189537 | 9/2011 |
| WO | WO 02/45718 * | 6/2002 |
| WO | 2004056738 | 7/2004 |

OTHER PUBLICATIONS

Mayo Clinic (1998), 10 pages.*
Tsikas et al (Blood, Mar. 22, 2012 _ vol. 119, No. 12).*
Arita et al. (2003). Mechanisms of enhanced apoptosis in HL-60 cells by UV-irradiated n-3 and n-6 polyunsaturated fatty acids. Free Radical Biology and Medicine, vol. 35, Issue 2, 189-199. (abstract only).
Bagga et al. (2003). Differential effects of prostaglandin derived from omega-6 and omega-3 polyunsaturated fatty acids on COX-2 expression and IL-6 secretion. Proc Natl Acad Sci U S A. 100(4):1751-6.
Brooks et al. (2008). Formation of highly reactive cyclopentenone isoprostane compounds (A3/J3-isoprostanes) in vivo from eicosapentaenoic acid. J Biol Chem. 2008, 283, 12043-12055.
Conti M. (2006). Cyclopentenone: a special moiety for anticancer drug design. Anticancer Drugs. 17(9):1017-22. (abstract only).
De Jong et al. (2011). "Anticancer Effects of 15d-Prostaglandin-J2 in Wild Type and Doxorubicin Resistant Ovarian Cancer Cells: Novel Actions on SIRT1 and HDAC" PLoS One vol. 6(9).
Emi and Maeyama. (2004). The biphasic effects of cyclopentenone prostaglandins, prostaglandin J(2) and 15-deoxy Delta(12,14)-prostaglandin J(2) on proliferation and apoptosis in rat basophilic leukemia (RBL-2H3) cells. Biochem Pharmacol. 1;67(7):1259-67. (abstract only).
Fukushima et al. (1989). Prostaglandin A and J: antitumor and antiviral prostaglandins. Adv Prostaglandin Thromboxane Leukot Res. 19:415-8. (abstract only).
Fukushima and Ryoho. (1983). [Development of antineoplastic prostaglandins]. [Article in Japanese] 10(9):1930-5. (abstract only).
Gandhi et al. (2011). Selenoprotein-dependent upregulation of hematopoietic prostaglandin D2 synthase in macrophages is mediated through the activation of peroxisome proliferator-activated receptor (PPAR) gamma. J. Biol. Chem. 286(31):27471-82. (abstract only).
Gao et al. (2007). Novel n-3 Fatty Acid Oxidation Products Activate Nrf2 by Destabilizing the Association between Keap and Cullin3. J. Biol. Chem., 282, 2529-2537.
Haslmayer et al. (2002). The peroxisome proliferator-activated receptor gamma ligand 15-deoxy-Delta12,14-prostaglandin J2 induces vascular endothelial growth factor in the hormone-independent prostate cancer cell line PC 3 and the urinary bladder carcinoma cell line 5637. Int J Oncol. 21(4):915-20. (abstract only).
Ishihara et al. (2004). Effect of prostaglandins on the regulation of tumor growth. Curr Med Chem Anticancer Agents. 4(4):379-87. (abstract only).
Khanim et al. (2009). "Combined Bezafibrate and Medroxyprogesterone Acetate: Potential Novel Therapy for Acute Myeloid Leukaemia" PLoS One vol. 4(12).

(Continued)

*Primary Examiner* — Shirley V Gembeh
(74) *Attorney, Agent, or Firm* — Novak Druce Connolly Bove + Quigg LLP

(57) ABSTRACT

Compositions, kits and methods for treating leukemia in a subject (e.g., human) include a first anti-cancer drug consisting of: $\Delta^{12}$-prostaglandin $J_3$ or a derivative thereof, or a prostaglandin D receptor (DP) agonist. The compositions may further include a second anti-cancer drug. $\Delta^{12}$-prostaglandin $J_3$ is a stable metabolite of omega-3 fatty acid, eicosapentaenoic acid (EPA), and was discovered to have anti-leukemic properties. $\Delta^{12}$-prostaglandin $J_3$ was shown to be highly effective in eradicating the leukemia stem cells (LSC) in two murine models of leukemia, thus increasing the survival of the mice. DP agonists were shown to induce apoptosis of human primary Acute Myelogenous Leukemia cells and may be used in compositions, kits and methods for treating leukemia in a subject. The compositions, kits and methods may be particularly useful for treating human subjects who are resistant to one or more anti-cancer drugs.

14 Claims, 26 Drawing Sheets

(56) References Cited

OTHER PUBLICATIONS

Kim et al. (1993). Prostaglandin A2 and D12-prostaglandin J2 induce apoptosis in L1210 cells. Fed Europ Biochem Soc, 321: 209-214. (abstract only).

Mullally et al. (2001). Cyclopentenone prostaglandins of the J series inhibit the ubiquitin isopeptidase activity of the proteasome pathway. J Biol Chem. 276(32):30366-73.

Musiek et al. (2005). Cyclopentenone isoprostanes inhibit the inflammatory response in macrophages J Biol Chem. 280(42):35562-70.

Musiek et al. (2008). Electrophilic cyclopentenone neuroprostanes are anti-inflammatory mediators formed from the peroxidation of the omega-3 polyunsaturated fatty acid docosahexaenoic acid. J Biol Chem 283, 19927-19935. (abstract only).

Ney PA. (2011). "The anti-leukemic activity of Δ12-PGJ3," Blood), vol. 118(26).

Prakash et al. (2009). "Albumin-Binding and Tumor Vasculature Determine the Antitumor Effect of 15 Deoxy-Delta12, 14-Prostaglandin-J2 in Vivo" Neoplasia vol. 11(12).

Primary products of fatty acid oxidation. Retrieved on: Nov. 29, 2012. Retrieved from: http://www.cyberlipid.org/perox/oxid0007.htm.

Rosetti et al. (2008). Pro-apoptotic activity of cyclopentenone in cancer cells. Anticancer Res. 28(1A):315-20. (abstract only).

Vosseler et al. (2003). Structural requirements of cyclopentenone prostaglandins to induce endothelial cell apoptosis. Biochem Biophys Res Commun. 25;307(2):322-6. (abstract only).

Hedge et al. (2011). Δ12-prostaglandin J3, an omega-3 fatty acid-derived metabolite, selectively ablates leukemia stem cells in mice. Blood. Dec. 22, 2011;118(26):6909-19.

Narumiya and Fukushima. (1985). Delta 12-prostoglandin, an ultimate metabolie of prostoglandin D2 exerting cell growth inhibition. (abtract only).

Wang and Mak. (2011). Induction of apoptosis in non-small cell lung carcinoma A549 cells by PGD2 metabolie, 15d-PGJ2.

Hayden et al. (2009). Treatment of primary CLL cells with bezafibrate and medroxyprogesteron acetate induces apoptosis and prepresses the pro-proliferative signal of CD40-ligand, in part through increased 15dΔ12, 14, PGJ2. Leukemia. 23: 292-304.

* cited by examiner

EFFECT OF Δ12-PGJ3 ON LSCs FROM AML AND BLAST-CRISIS CML PATIENTS

| PATIENT ID | TOTAL NUMBER OF CELLS PLATED | CD34+ CELLS (%) | % OF CD34+ CELLS THAT ARE CD38- CD123+ (LSCs) | LSCs UNDERGOING APOPTOSIS (%) | APOPTOSIS OF LSCs UPON PRETREATMENT WITH CAY10471 (%) |
|---|---|---|---|---|---|
| AML100810_V1 | 110,000 | 28 | 82 | 83 | 4 |
| AML123009_V1 | 110,000 | 34 | 92 | 89 | 7 |
| AML033107 | 110,000 | 27 | 92 | 90 | 4 |
| AML041909 | 110,000 | 34 | 94 | 92 | 5 |
| AML101308 | 110,000 | 29 | 92 | 89 | 4 |

FIG. 15

COMPOSITIONS, METHODS AND KITS FOR TREATING LEUKEMIA

FEDERALLY SPONSORED RESEARCH

This invention was made with government support under Hatch Act Project No. PEN04202, awarded by the United States Department of Agriculture/NIFA. The Government has certain rights in the invention.

CROSS-REFERENCE TO RELATED APPLICATIONS

This application claims the benefit of U.S. Provisional Application Ser. No. 61/502,677, filed Jun. 29, 2011, U.S. Provisional Application Ser. No. 61/535,149, filed Sep. 15, 2011, and U.S. Provisional Application Ser. No. 61/635,458, filed Apr. 19, 2012, all of which are hereby incorporated by reference in their entireties, for all purposes, herein.

FIELD OF THE INVENTION

The invention relates generally to the fields of molecular genetics, molecular biology, and oncology.

BACKGROUND

Leukemia is a highly prevalent disease that signifies uncontrolled production of white blood cells. Currently, there is no cure for leukemia. Current therapies of leukemia include chemotherapy, radiation therapy, stem cell therapy, and biological therapy. All of these therapies suffer from many side effects. Use of anti-leukemic drugs only prolong the life of the patient by targeting the bulk cancer cells, but not the cancer stem cells.

SUMMARY

Described herein are compositions, methods and kits for treating cancers such as leukemia. Targeting cancer stem cells (CSC) is of paramount importance to successfully combat the relapse of cancer. It is shown herein that $\Delta^{12}$-PGJ$_3$, a novel and naturally produced cyclopentenone prostaglandin, CyPG, from the dietary fish-oil omega-3 polyunsaturated fatty acid (n-3 PUFA), eicosapentaenoic acid (EPA; 20:5), alleviates the development of leukemia in two well-studied murine models of leukemia. Intraperitoneal administration of $\Delta^{12}$-PGJ$_3$ to mice infected with Friend erythroleukemia virus (FV) or those expressing chronic myelogenous leukemia (CML) oncoprotein BCR-ABL in the hematopoietic stem cell (HSC) pool completely restored normal hematological parameters, splenic histology, and enhanced the survival of such mice. More importantly, $\Delta^{12}$-PGJ$_3$ selectively targeted leukemia stem cells (LSC) for apoptosis in the spleen and bone marrow. This treatment completely eradicated LSCs in vivo as demonstrated by the inability of donor cells from treated mice to cause leukemia in secondary transplants. This is the first example of a compound that eradicates leukemia stem cells and effectively "cures" CML in a mouse model and prolongs the life of the leukemic mice indefinitely. Given the potency of n-3 PUFA-derived CyPG and the well-known refractoriness of LSC to currently used clinical agents, $\Delta^{12}$-PGJ$_3$ represents a new chemotherapeutic for leukemia that targets LSCs.

Accordingly, described herein is a composition including a therapeutically effective amount of a first anti-cancer drug, the first anti-cancer drug being isolated or synthesized $\Delta^{12}$-PGJ$_3$ or a derivative thereof, for inhibiting LSC growth in a subject having LSCs (e.g., a subject suffering from leukemia) and a pharmaceutically acceptable carrier. The composition can further include a second anti-cancer drug (e.g., imatinib (Gleevec® Novartis, East Hanover, N.J.)).

Also described herein is a composition including a therapeutically effective amount of a first anti-cancer drug that is an isolated or synthesized prostaglandin D receptor (DP) agonist for inhibiting LSC growth in a subject having LSCs and a pharmaceutically acceptable carrier. The composition can further include a second anti-cancer drug (e.g., imatinib). The DP agonist can be, for example, one or more of: $\Delta^{12}$-PGJ$_3$, ZK118182, and PGD2ME.

Further described herein is a method of treating leukemia in a subject. The method includes administering to the subject having leukemia a composition including a therapeutically effective amount of a first anti-cancer drug that is one or more of: isolated or synthesized $\Delta^{12}$-PGJ$_3$ or a derivative thereof, a derivative of prostaglandin D3, and an isolated or synthesized DP agonist, for inducing death of LSCs in the subject. The LSCs can be, for example, chronic myeloid leukemia stem cells or acute myeloid leukemia cells. In some embodiments, the subject is resistant to an anti-cancer drug (e.g., imatinib). In the method, the composition can further include a therapeutically effective amount of a second anti-cancer drug (e.g., imatinib, standard chemotherapy agents such as cytarabine or doxorubicin, etc.).

Yet further described herein is a method of treating leukemia in a subject (e.g. human). The method includes administering to the subject having leukemia a composition including a therapeutically effective amount of a DP agonist for inducing death of LSCs in the subject. The LSCs can be, for example, chronic myeloid leukemia stem cells. In some embodiments, the subject is resistant to imatinib. In the method, the composition can further include a therapeutically effective amount of an anti-cancer drug (e.g., imatinib, standard chemotherapy agents such as cytarabine or doxorubicin, etc.).

Additionally described herein is a kit for treating leukemia in a subject (e.g., human). The kit includes a composition including a therapeutically effective amount of a first anti-cancer drug that is one of: an isolated or synthesized DP agonist, an isolated or synthesized $\Delta^{12}$-PGJ$_3$, and a derivative of $\Delta^{12}$-PGJ$_3$, for inducing death of LSCs in the subject; instructions for use, and packaging. The kit can further include a second anti-cancer drug (e.g., imatinib, standard chemotherapy agents such as cytarabine or doxorubicin, etc.).

Unless otherwise defined, all technical terms used herein have the same meaning as commonly understood by one of ordinary skill in the art to which this invention belongs.

As used herein, "protein" and "polypeptide" are used synonymously to mean any peptide-linked chain of amino acids, regardless of length or post-translational modification, e.g., glycosylation or phosphorylation.

By the term "gene" is meant a nucleic acid molecule that codes for a particular protein, or in certain cases, a functional or structural RNA molecule.

As used herein, a "nucleic acid" or a "nucleic acid molecule" means a chain of two or more nucleotides such as RNA (ribonucleic acid) and DNA (deoxyribonucleic acid).

The terms "patient," "subject" and "individual" are used interchangeably herein, and mean a mammalian (e.g., human, rodent, non-human primates, canine, bovine, ovine, equine, feline, etc.) subject to be treated and/or to obtain a biological sample from.

As used herein, "bind," "binds," or "interacts with" means that one molecule recognizes and adheres to a particular second molecule in a sample or organism, but does not substantially recognize or adhere to other structurally unrelated molecules in the sample. Generally, a first molecule that "specifically binds" a second molecule has a binding affinity greater than about $10^{-8}$ to $10^{-12}$ moles/liter for that second molecule and involves precise "hand-in-a-glove" docking interactions that can be covalent and noncovalent (hydrogen bonding, hydrophobic, ionic, and van der waals).

The term "labeled," with regard to a probe or antibody, is intended to encompass direct labeling of the probe or antibody by coupling (i.e., physically linking) a detectable substance to the probe or antibody.

When referring to a nucleic acid molecule or polypeptide, the term "native" refers to a naturally-occurring (e.g., a wild type or WT) nucleic acid or polypeptide.

As used herein, the term "regulating", "regulation", "modulating" or "modulation" refers to the ability of an agent to either inhibit or enhance or maintain activity and/or function of a molecule (e.g., a receptor). For example, an inhibitor of a DP would down-regulate, decrease, reduce, suppress, or inactivate at least partially the activity and/or function of the DP. Up-regulation refers to a relative increase in function and/or activity.

By the term "$\Delta^{12}$-PGJ$_3$" is meant $\Delta^{12}$-prostaglandin J$_3$, an omega-3 fatty acid-derived metabolite.

By the phrase "Dagonist" is meant any agent (e.g., drug, compound, hormone, etc.) that forms a complex with or binds to a DP site on a cell, thereby triggering an active response from the cell. DP agonists can be naturally occurring or synthetic, or a combination thereof.

By the phrase "leukemia stem cells" is meant leukemia initiating cells that are functionally defined to possess the property to generate more leukemia stem cells (self renewal) and non-stem cell leukemia cells. Additionally, these cells are characterized by the expression of certain cell surface markers, which include but are not limited to CD34, CD123, and CD117.

The phrases "isolated" or biologically pure" refer to material, which is substantially or essentially free from components which normally accompany it as found in its native state.

The term "antibody" is meant to include polyclonal antibodies, monoclonal antibodies (mAbs), chimeric antibodies, humanized antibodies, anti-idiotypic (anti-Id) antibodies to antibodies that can be labeled in soluble or bound form, as well as fragments, regions or derivatives thereof, provided by any known technique, such as, but not limited to, enzymatic cleavage, peptide synthesis or recombinant techniques.

As used herein, the terms "diagnostic," "diagnose" and "diagnosed" mean identifying the presence or nature of a pathologic condition (e.g., leukemia).

The term "sample" is used herein in its broadest sense. A sample including polynucleotides, polypeptides, peptides, antibodies and the like may include a bodily fluid, a soluble fraction of a cell preparation or media in which cells were grown, genomic DNA, RNA or cDNA, a cell, a tissue, skin, hair and the like. Examples of samples include saliva, serum, blood, urine and plasma.

As used herein, the term "treatment" is defined as the application or administration of a therapeutic agent to a patient, or application or administration of the therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease. Treatment can include, for example, ameliorating, preventing or eliminating splenomegaly, reducing the number of LSCs in a subject, eliminating LSCs in a subject, etc.

As used herein, the term "safe and effective amount" refers to the quantity of a component, which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a composition of the present invention effective to yield the desired therapeutic response. For example, an amount effective to delay the growth of or to cause a cancer (e.g., CML) to shrink or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

Although compositions, kits, and methods similar or equivalent to those described herein can be used in the practice or testing of the present invention, suitable compositions, kits, and methods are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

FIG. 15 is a Table listing the effect of $\Delta^{12}$-PGJ$_3$ on LSCs from AML and blast-crisis CML patients.

DETAILED DESCRIPTION

Figure 1A:
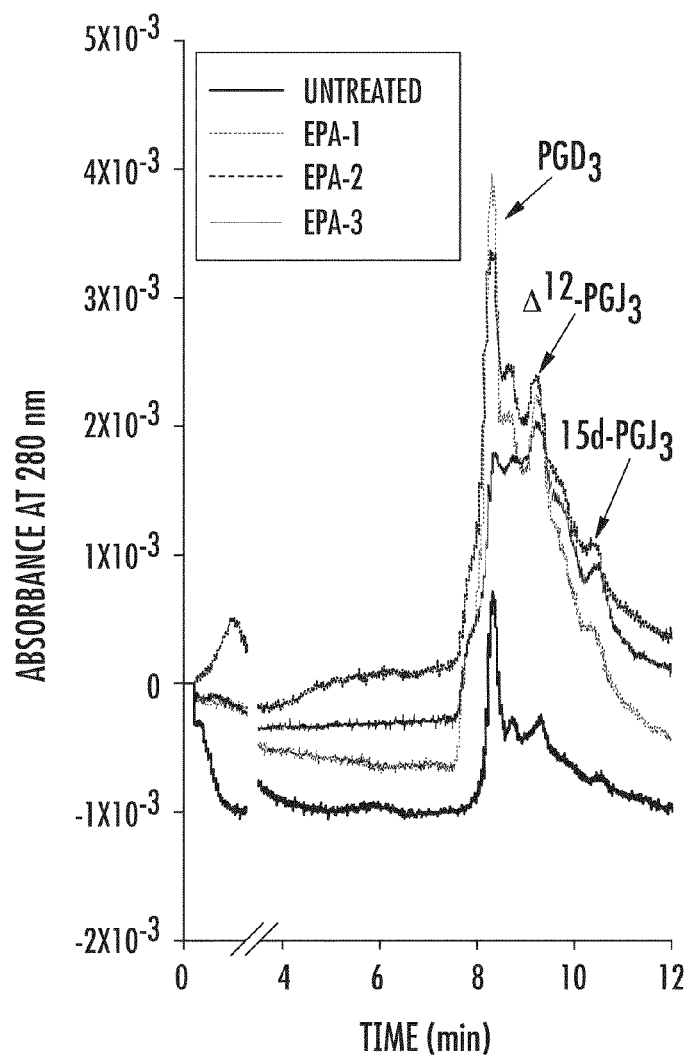
FIG. 1 shows endogenous production and pro-apoptotic properties of $\Delta^{12}$-PGJ$_3$. (A) Endogenous formation of PGD$_3$, PGJ$_3$, 15d-PGJ$_3$ in RAW264.7 macrophages, LC-UV trace; N=3 for EPA treated. (B) Representative LC-MS of $\Delta^{12}$-PGJ$_3$ containing eluates with characteristic fragmentation pattern is shown. (C) Dose-response demonstrating the effect of $\Delta^{12}$-PGJ$_3$ on BCR-ABL$^+$LSC compared with normal HSCs (MSCV-GFP$^+$HSC). Cells were treated ex vivo with $\Delta^{12}$-PGJ$_3$ for 36 h. Apoptosis was measured by annexin V staining. (D) Kit$^+$Sca-1$^+$Lin$^-$BCR-ABL-GFP$^+$ cells sorted from the bone marrow and cultured ex vivo in media containing $\Delta^{12}$-PGJ$_3$ (25 nM) or vehicle control for 36 h followed by flow cytometric analysis of GFP$^+$ cells. N=3; Mean±s.e.m. shown. *p<0.005. Expressed as percent of input GFP$^+$ cells. (E) Dose response of LSCs isolated from FV mice with indicated concentrations of $\Delta^{12}$-PGJ$_3$ at the end of 36 h of incubation. Apoptosis of LSCs was examined by Annexin V staining followed by flow cytometry. (F) FV-LSCs were cultured ex vivo with 25 nM of each compound for 36 h. N=3; Mean±s.e.m. shown *P<0.0001 (compared to PGJ$_3$).

AML is one of the most common types of leukemia in adults. Unfortunately, the five year relative survival rates for AML are the lowest when compared to other forms of leukemia. AML is a stem cell disease where LSCs occupy the apex of the disease hierarchy. LSCs can self renew and generate non-stem cell progeny that make up the bulk of the leukemia cells. Although chemotherapy agents can effectively target bulk leukemia cells, LSCs have active mechanisms to avoid killing by these drugs. As a consequence, failure to eliminate LSCs results in relapse of the disease. Because of this property, specific targeting of LSCs is essential for successful treatment. Although the need for new anti-LSC based therapies is well recognized, the identification of mechanism-based drugs to target LSCs has been lacking. Clearly new approaches are needed. Described herein are compositions, methods and kits for treating cancer (e.g., leukemia). A metabolite derived from ω-3 fatty acids, $\Delta^{12}$PGJ$_3$, was discovered which effectively eradicates LSCs in two mouse models of chronic leukemia. In the experiments described herein, these findings were extended to show that $\Delta^{12}$-PGJ$_3$ effectively targets AML LSCs by inducing apoptosis in murine models of AML and in human AML leukemia samples. In contrast, PGJ$_3$ has no effect on normal hematopoietic stem cells or the differentiation of hematopoietic progenitors. $\Delta^{12}$-PGJ$_3$ acts by inducing the expression of p53 in LSCs and leukemia cells. High-level expression of p53 in LSCs is incompatible with self renewal and leads to apoptosis. These data suggest that $\Delta^{12}$-PGJ$_3$ is a chemotherapeutic agent for treating AML. This is the first example of a compound that eradicates leukemia stem cells and effectively "cures" CML in a mouse model and prolongs the life of the leukemic mice indefinitely.

Biological Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates).

Compositions for Treating Leukemia in a Subject

Described herein are compositions for treating leukemia in a subject (e.g., a human subject). Examples of leukemias that can be treated using the compositions include Acute Myelogenous Leukemia (AML), CML, Acute Lymphocytic Leukemia (ALL) and Chronic Lymphocytic Leukemia (CLL). In one embodiment, a composition includes a therapeutically effective amount of $\Delta^{12}$-prostaglandin $J_3$, or a derivative thereof (a first anti-cancer drug), for inhibiting LSC growth in a subject having LSCs, and a pharmaceutically acceptable carrier. Inhibiting LSC growth includes inducing death (killing of) of the cancer cells, and/or inducing differentiation of the cancer cells (promoting a more differentiated phenotype, e.g., causing differentiation of LSCs into terminally differentiated cells). Any suitable form of $\Delta^{12}$-prostaglandin $J_3$ or derivative thereof can be used (e.g., synthesized, isolated). $\Delta^{12}$-prostaglandin $J_3$ derivatives that may find particular use in the compositions and methods described herein are those that induce apoptosis or differentiation of LSCs (e.g., 16,16-dimethyl-$\Delta^{12}$-$PGJ_3$). In such embodiments, when administered to a subject, the composition induces apoptosis of LSCs. The composition can further include one or more additional anti-cancer drugs (e.g., a second anti-cancer drug). Examples of additional anti-cancer drugs include imatinib, nilotinib, dasafanib, new generation BCR-ABL inhibitors, and standard chemotherapy drugs such as cytarabine or doxorubicin or similar classes of drugs. In one embodiment, a combination therapy including imatinib or a new generation BCR-ABL inhibitor and $\Delta^{12}$-$PGJ_3$ may be particularly therapeutic.

In another embodiment, a composition includes a therapeutically effective amount of a DP agonist (a first anti-cancer drug) for inhibiting LSC growth in a subject having LSCs and a pharmaceutically acceptable carrier. Examples of DP agonists include a small molecule, a protein, a peptide, a polynucleotide, an oligonucleotide, an organic compound, an inorganic compound, synthetic compounds or compounds isolated from unicellular or multicellular organisms. Specific examples of DP agonists include $PGD_2ME$ (Prostaglandin $D_2$ methyl ester (9α,15S-dihydroxy-[1-oxo-prosta-5Z,13E-dien-1-oic acid, methyl ester) and ZK118182 ([[4-[5R-chloro-2Z-[3R-cyclohexyl-3S-hydroxy-1R-propenyl]-3S-hydroxycyclopentyl]-2R-butenyl]oxy]-acetic acid, isopropyl ester). An agonist of a DP is any agent that activates the DP. Any agent that activates DP can be used in compositions and methods described herein for inducing death of LSCs and treating leukemia. A composition including a DP agonist can further include one or more additional anti-cancer drugs (e.g., a second anti-cancer drug). As noted above, examples of additional anti-cancer drugs include imatinib, nilotinib, dasa-tanib, new generation BCR-ABL inhibitors, standard chemotherapy drugs such as cytarabine or doxorubicin, etc.

In the compositions described herein, $\Delta^{12}$-prostaglandin $J_3$ can be obtained commercially or synthesized according to the methods described, for example, in the Examples section below. Similarly, $\Delta^{12}$-prostaglandin $J_3$ derivatives can be synthesized as described by Kimball et al. (Kimball F A, Bundy G L, Robert A, and Weeks J R (1979), Synthesis and biological properties of 9-deoxo-16, 16-9-methylene-$PGE_2$. Prostaglandins 17: 657-66).

Effective Doses

The compositions described above are preferably administered to a mammal (e.g., rodent, human, non-human primates, canine, bovine, ovine, equine, feline, etc.) in an effective amount, that is, an amount capable of producing a desirable result in a treated subject (e.g., inhibiting growth of LSCs and/or inducing death of LSCs in the subject). Toxicity and therapeutic efficacy of the compositions utilized in methods of the invention can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms of the cancer and other drugs being administered concurrently. A composition as described herein is typically administered at a dosage that induces death of LSCs (e.g., induces apoptosis of LSCs), as assayed by identifying a reduction in hematological parameters (Complete blood count (CBC)), or cancer cell growth or proliferation. In the experiments described herein, the amount of $\Delta^{12}$-$PGJ_3$ used to eradicate LSCs was calculated to be 0.6 micrograms/day/gram mouse for 7 days. Generally, the dose is in mg/Kg subject/day=ug/g subject/day. In a typical embodiment, a dose in the range of about 0.025 to about 0.05 mg/Kg/day is administered. Such a dose is typically administered once a day for a few weeks.

Methods of Treating Cancer

Described herein are methods of treating cancer (e.g., leukemia) and/or disorders or symptoms thereof. The methods include administering a therapeutically effective amount of a pharmaceutical composition including a pharmaceutically acceptable carrier and an amount of $\Delta^{12}PGJ_3$, a derivative thereof, or a DP agonist (a first anti-cancer drug) sufficient to treat the disease or disorder or symptom thereof to a subject (e.g., a mammal such as a human). In the method, an amount of $\Delta^{12}$-$PGJ_3$, a derivative thereof, or a DP agonist sufficient to induce death of LSCs in the subject is typically administered. In a typical embodiment, the LSCs are CML stem cells. In some embodiments, the composition can be administered to a subject who is resistant to imatinib or other anti-cancer drug. In the methods, the composition can further include a therapeutically effective amount of one or more additional anti-cancer drugs (e.g., a second anti-cancer drug such as imatinib) or standard chemotherapy.

The therapeutic methods of the invention (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for a disease, disorder, or symptom thereof. Determination of those subjects "at risk"

can be made by any objective or subjective determination by a diagnostic test or opinion of a subject or health care provider (e.g., genetic test, enzyme or protein marker, marker (as defined herein), family history, and the like).

The administration of a composition including $\Delta^{12}$-PGJ$_3$, a derivative thereof, or a DP agonist for the treatment of cancer (e.g., leukemia) may be by any suitable means that results in a concentration of the therapeutic that, (e.g., when combined with other components), is effective in ameliorating, reducing, or stabilizing a cancer. The $\Delta^{12}$-PGJ$_3$, a derivative thereof, or a DP agonist may be contained in any appropriate amount in any suitable carrier substance, and is generally present in an amount of 1-95% by weight of the total weight of the composition. The composition may be provided in a dosage form that is suitable for local or systemic administration (e.g., parenteral, subcutaneously, intravenously, intramuscularly, or intraperitoneally). The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Compositions as described herein may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a cancer, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

As indicated above, the pharmaceutical compositions described herein may be in a form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Materials for use in the preparation of microspheres and/or microcapsules are, e.g., biodegradable/bioerodible polymers such as polygalactin, poly-(isobutyl cyanoacrylate), poly(2-hydroxyethyl-L-glutam-nine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Formulations for oral use include tablets containing the active ingredient(s) (e.g., $\Delta^{12}$-PGJ$_3$ or a derivative thereof, a DP agonist) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

Optionally, a composition as described herein may be administered in combination with any other anti-cancer therapy (e.g., imatinib); such methods are known to the skilled artisan and described in Remington: The Science and Practice of Pharmacy, supra. In one example, an effective amount of $\Delta^{12}$-PGJ$_3$, a derivative thereof, or a DP agonist is administered in combination with radiation therapy. Combinations are expected to be advantageously synergistic. Therapeutic combinations that inhibit cancer (e.g., leukemia) cell growth and/or induce apoptosis of LSCs are identified as useful in the methods described herein.

In one embodiment, the invention provides a method of monitoring treatment progress. The method includes the step of determining a level of changes in hematological parameters and LSC analysis with cell surface proteins as diagnostic markers (which can include, for example, but are not limited to CD34, CD38, CD90, and CD117) or diagnostic measurement (e.g., screen, assay) in a subject suffering from or susceptible to a disorder or symptoms thereof associated with cancer (e.g., leukemia) in which the subject has been administered a therapeutic amount of a composition as described herein. The level of marker determined in the method can be compared to known levels of marker in either healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

Kits for Treating Leukemia in a Subject

Described herein are kits for treating leukemia in a subject. A typical kit includes a composition including a therapeutically effective amount of a DP agonist or of $\Delta^{12}$-prostaglandin J3 or a derivative thereof (a first anti-cancer drug) for inducing death of LSCs in a subject, packaging, and instructions for use. In a kit, the composition may further include a pharmaceutically acceptable carrier in unit dosage form. If desired, the kit also contains an effective amount of an additional anti-cancer drug (e.g., a second anti-cancer drug such as imatinib). In some embodiments, the kit includes a sterile container which contains a therapeutic or prophylactic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

EXAMPLES

The present invention is further illustrated by the following specific examples. The examples are provided for illustration only and should not be construed as limiting the scope of the invention in any way.

Example 1

$\Delta^{12}$-Prostaglandin J$_3$, an Omega-3 Fatty Acid-Derived Metabolite, Selectively Ablates LSCs in Mice The endogenous formation of $\Delta^{12}$-PGJ$_3$ from EPA was investigated and the ability of this novel n-3 PUFA metabolite to target LSCs was examined in two well-studied models of leukemia, Friend Virus (FV)-induced erythroleukemia (Ben-David Y & Bernstein A, Cell. 1991; 66:831-834) and a well-established model for inducing CML in mice, which utilizes BCR-ABL-IRESGFP retrovirus (Schemionek M et al., Blood. 2010; 115:3185-3195; Pear W S et al., Blood. 1998; 92:3780-3792; Hu Y et al., Proc Natl Acad Sci USA. 2006; 103:16870-16875; Zhao C et al., Nature. 2009; 458:776-779), wherein transplantation of transduced HSCs into mice results in pathology similar to the chronic phase of CML. FV-induces leukemia by activating the bone morphogenetic protein-4 (BMP4)-dependent stress erythropoiesis pathway, which leads to a rapid amplification of target cells and acute disease (Subramanian A et al., J. Virol. 2008; 82:382-393). The results described herein demonstrate that $\Delta^{12}$-PGJ$_3$ administration (at doses as low as 0.6 µg/g mouse/day) to FV-infected and BCR-ABL$^+$ transduced HSC (hereafter referred to as BCR-ABL$^+$ LSC) transplanted mice completely ablates leukemia, restores the hematological parameters, and eradicates LSC via the activation of ATM/p53 pathway of apoptosis in these cells.

METHODS

Cell culture. Murine erythroleukemia (MEL) cells were cultured in DMEM with 10% FBS. In order to examine the production 3-series PGs, BALB/c-derived RAW264.7 macrophage-like cells (ATCC) were cultured in DMEM containing 5% FBS, 250 nM sodium selenite, and 50 µM EPA (as BSA conjugate) for 72 h followed by stimulation with E. coli endotoxin lipopolysaccharide (LPS; Serotype 0111B4; 50 ng/ml) for 30 min. The cells were cultured in fresh DMEM for an additional 24-144 h. Cells cultured with cell culture-grade fatty acid free BSA (Sigma Aldrich) served as a control. Culture media was withdrawn at various times and analyzed for 3-series PGs as described below. Total RNA was isolated from cells or tissues using Trizol reagent as per the instructions of the supplier (Invitrogen, Carlsbad, Calif.) and cDNA was prepared using a High Capacity cDNA Reverse Transcriptase kit (Applied Biosystems, Foster City, Calif.). Semi-quantitative RT-PCR for p53 and β-actin was performed with primers as described in Supplementary Methods. Nuclear and cytoplasmic protein extracts of LSCs were prepared using standard methods previously described (Vunta H et al., J Biol. Chem. 2007; 282:17964-17973).

Preparation, isolation, and spectroscopic characterization of PGD$_3$ metabolites. PGD$_3$ (Cayman Chemicals) was incubated with 0.1 M sodium phosphate buffer, pH 7.4, containing 0.9% NaCl at a final concentration of 100 µg/ml with shaking at 37° C. for varying periods (24 h-144 h). The reaction products and those from the cell culture media supernatants were purified by HPLC and analyzed by UV and MS as described below in Supplementary Information and Methods.

Apoptosis. Apoptosis of LSCs was performed using annexin V as described below in Supplementary Information and Methods.

FV-induced erythroleukemia and production of FV leukemia stem cells (FV-LSCs): BALB/c mice were infected with FV as previously described (Subramanian A et al., J. Virol. 2008; 82:382-393; Harandi O F et al., J Clin Invest. 2010; 120:4507-4519). On day 14 after infection, spleens were isolated and a single cell suspension of spleen cells was generated. The cells were filtered through a 70 µm sterile filter and flow-through cells were resuspended in RBC lysis buffer followed by centrifugation. Leukemia stem cells were isolated by FACS. Spleen cells were labeled with anti-Kit, Sca1 (BioLegend, San Diego, Calif.) and M34 antibodies. M34 is a monoclonal antibody that recognizes the envelope protein of SFFV (Chesebro B et al., Virology. 1981; 112:131-144) and was used as previously described (Subramanian A et al., J. Virol. 2008; 82:382-393). As indicated M34$^+$Kit+Sca1+ cells were cultured in Methocult media (Stem Cell Technologies Vancouver BC) M3334 supplemented with 200 ng/ml Sonic Hedgehog (Shh), 15 ng/ml bone morphogenetic protein-4 (BMP4) (both from R&D Systems Minneapolis, Minn.), and 50 ng/ml stem cell factor (SCF; Peprotech). For CFU-FV assays, cells were plated in methylcellulose media containing fetal calf serum, but lacking added growth factors as previously described (Mager D L et al., Proc Natl Acad Sci USA. 1981; 78:1703-1707).

Transplant of FV-LSCs into BALB/c-Stk$^{-/-}$ mice: FV-LSCs were generated as described above. 2.5×10$^5$ FV-LSCs were transplanted into BALB/c-Stk$^{-/-}$ mice by retro-orbital injection. Six weeks after transplant the mice were treated with CyPGs or vehicle control as indicated in the text.

Induction of CML using MIGR-BCR-ABL retrovirus: MIGR-BCR-ABL and control MSCV-GFP retroviruses were obtained. Viral stocks were generated in HEK293 cells as previously described (Finkelstein L et al., Oncogene. 2002; 21:3562-3570). C57BL/6 mice were treated with 5-fluorouracil (5-FU; 150 mg/Kg, Sigma, St. Louis, Mo.) to enrich for cycling HSCs. On day four after treatment bone marrow cells were harvested and infected with MIGR-BCR-ABL or MSCV-GFP control virus overnight in IMDM media containing 5% FCS and supplemented with 2.5 ng/ml IL-3 and 15 ng/ml SCF (R&D Systems Minneapolis, Minn.). $0.5 \times 10^6$ transduced cells were transplanted by retro-orbital injection into C57BL/6 recipient mice that were preconditioned with 950 Rads of irradiation. In order to increase the number of CML and control mice, 17 days after transplant GFP$^+$spleen cells were isolated by FACS and $1 \times 10^5$ GFP$^+$ cells were transplanted into irradiated (950 Rads) secondary C57BL/6 recipients. Two weeks after transplant, mice were treated as indicated with CyPGs and vehicle control. For ex-vivo experiments, Kit$^+$Sca1$^+$Lin$^-$GFP$^+$cells were isolated from the bone marrow or spleen of transplanted mice by FACS. The sorted cells were cultured in Methocult media M3334 (Stem Cell Technologies Vancouver BC) M3334 supplemented with Shh, SCF, and BMP4 and treated with the indicated CyPGs and vehicle controls for indicated time periods. To demonstrate the effect of $\Delta^{12}$-PGJ$_3$ on normal hematopoietic progenitors, HSCs isolated from the bone marrow of C57BL/6 mice were cultured in methylcellulose media ($1 \times 10^6$ cells/ml/well) containing Epo (3 U/ml), SCF, IL-3, and BMP4 in the presence or absence of $\Delta^{12}$-PGJ$_3$ (25 nM). The hematopoietic colonies (colony forming cells in culture, CFC) were scored.

Secondary transplants to test for residual LSCs after treatment with $\Delta^{12}$-PGJ$_3$: For the CML model, B6.5JLPtprca Pep3b/BoyJ (CD45.1$^+$) mice were treated with 5-FU and bone marrow cells enriched in cycling HSCs were isolated followed by infection with MIGR-BCR-ABL virus or control MSCV-GFP virus as described above. The cells were transplanted into C57BL/6 (CD45.2) recipient mice as mentioned earlier. The mice were treated with $\Delta^{12}$-PGJ$_3$ or vehicle control as indicated. Two weeks after treatment, spleen cells were isolated and transplanted into irradiated secondary C57BL/6 (CD45.2) recipients as described above. Two weeks after secondary transplant, mice were analyzed for WBC counts, splenomegaly and the presence of GFP$^+$ or CD45.1 donor cells in the bone marrow and spleen by flow cytometry. Secondary transplants were also done with FV infected mice treated with $\Delta^{12}$-PGJ$_3$ or vehicle control. BALB/c mice were infected with Friend virus as described above. The mice were treated with $\Delta^{12}$-PGJ$_3$ or vehicle control as indicated. Two weeks after treatment, spleen cells isolated from FV-infected mice and transplanted into BALB/c-Stk$^{-/-}$ recipient mice ($1 \times 10^5$ cells per mouse). Five weeks post transplant, the mice with secondary transplants were tested for WBC counts, splenomegaly and for the presence of M34$^+$Kit$^+$Sca1$^+$FV-LSCs by flow cytometry.

Treatment of Mice with PGs: Mice with FV-induced erythroleukemia or MIGR-BCR-ABL induced CML were treated on the indicated days with CyPGs. Mice were treated with a daily intraperitoneal injection of $\Delta^{12}$-PGJ$_3$ (0.01-0.1 mg/kg), 15d-PGJ$_2$ (0.1 mg/kg), or 9,10-dihydro-15d-PGJ$_2$ (0.1 mg/kg) for 7 days. All three compounds were formulated with hydroxypropyl-β-cyclodextrin (30% w/v; Sigma; vehicle control). All experiments utilizing mice were approved by the IACUC of the Pennsylvania State University.

Inhibition of ATM kinase in LSC. LSCs isolated from FV-infected mice or BCR-ABL$^+$LSCs transplanted mice were treated with indicated concentrations of either ATM-specific inhibitor (MTPO, 2-Morpholin-4-yl-6-thianthren-1-yl-pyran-4-one; KU55933; 50 nM; Calbiochem) or ATM/ATR-specific inhibitor (CGK-733; 1 μM; Calbiochem) followed by treatment with CyPGs.

Statistical analysis. The results are expressed as means±s.e.m. and the differences between groups were analyzed using Student's t test using GraphPad Prism. The criterion for statistical significance was P<0.05.

RESULTS

Figure 1B:
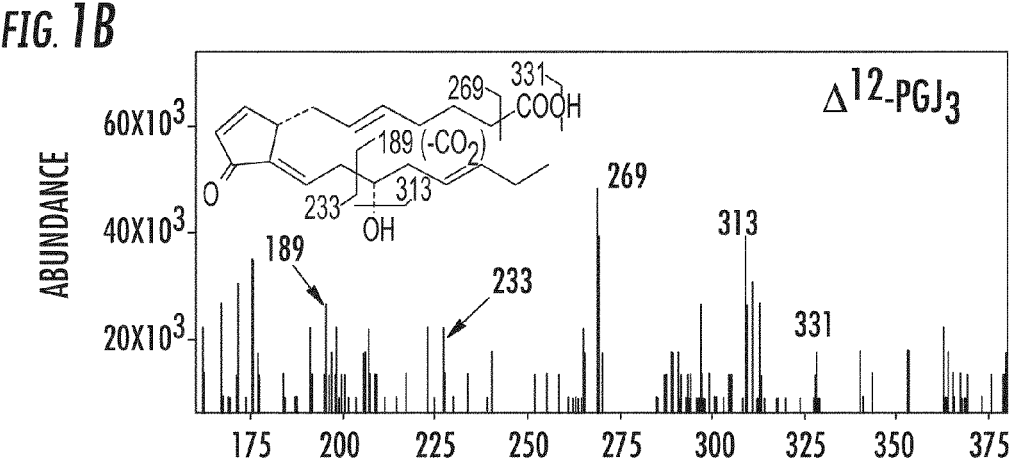
Figure 6A:
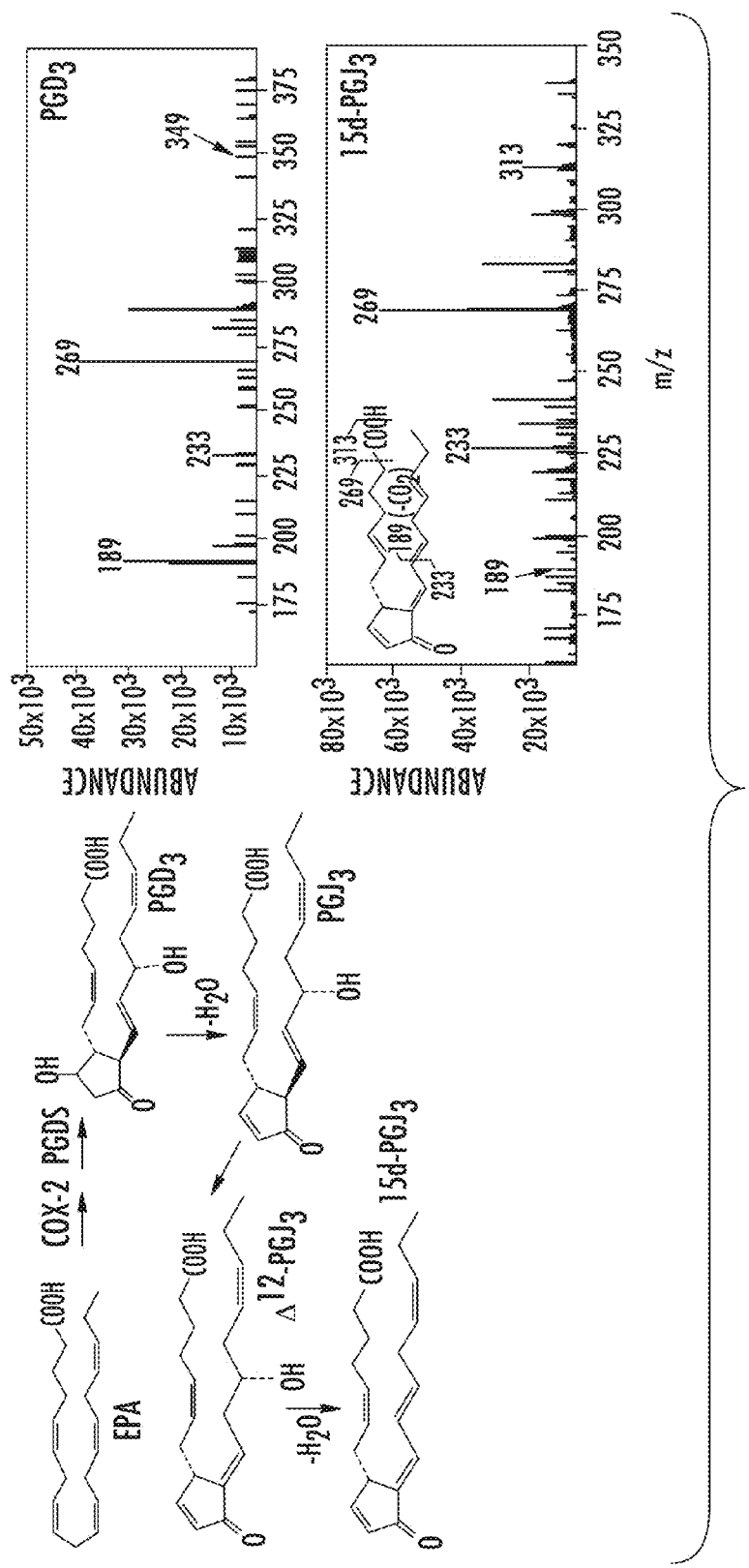
FIG. 6 shows spontaneous conversion of PGD$_3$ to PGJ$_3$, $\Delta^{12}$-PGJ$_3$, and 15d-PGJ$_3$ in-vitro.
Figure 6B:
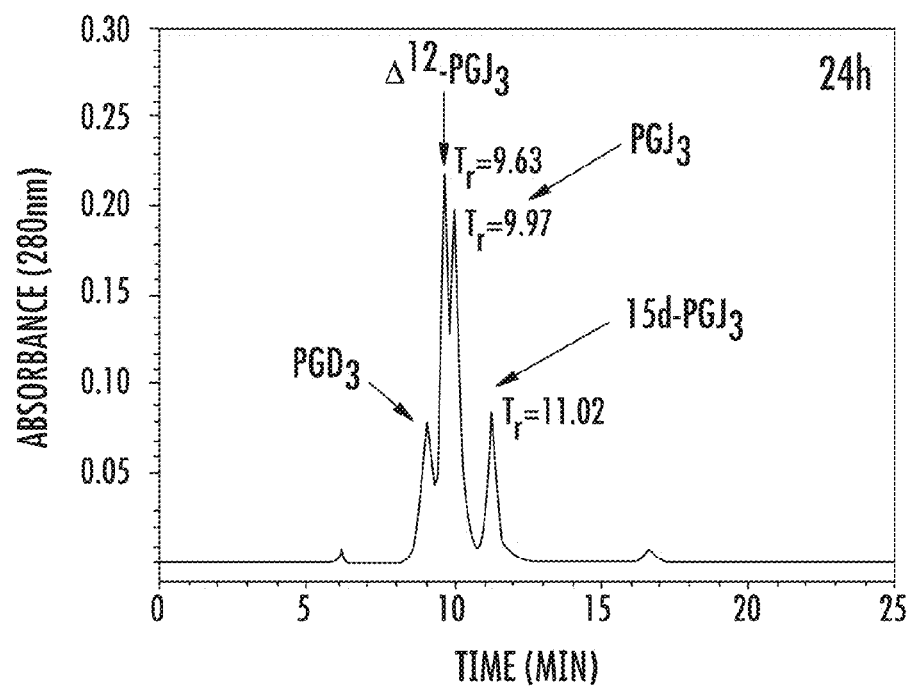
Figure 6C:
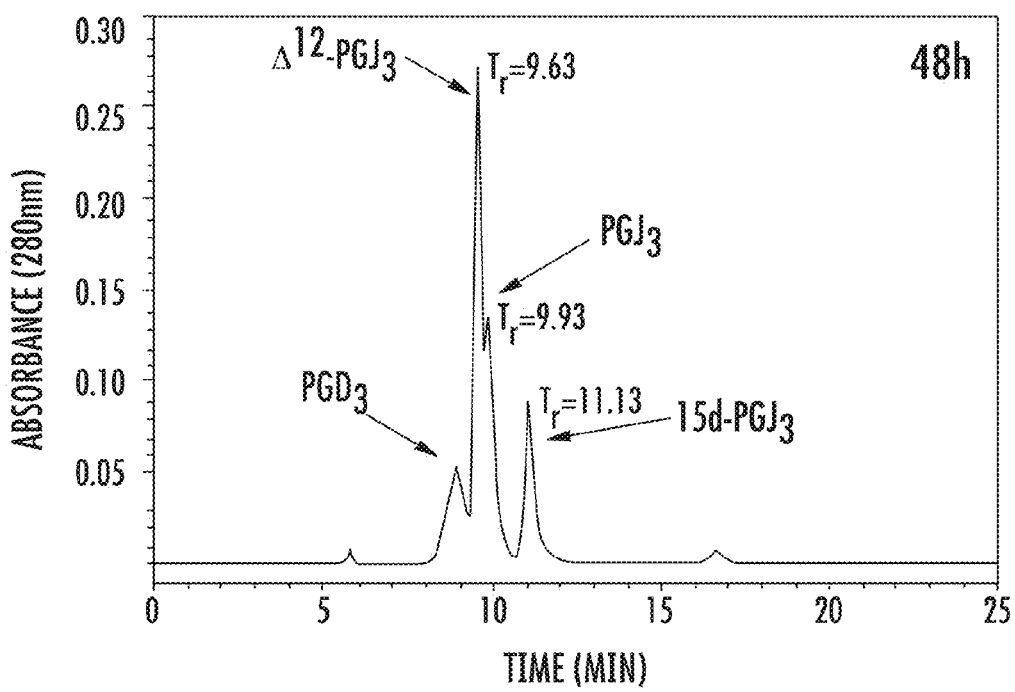
Figure 6D:
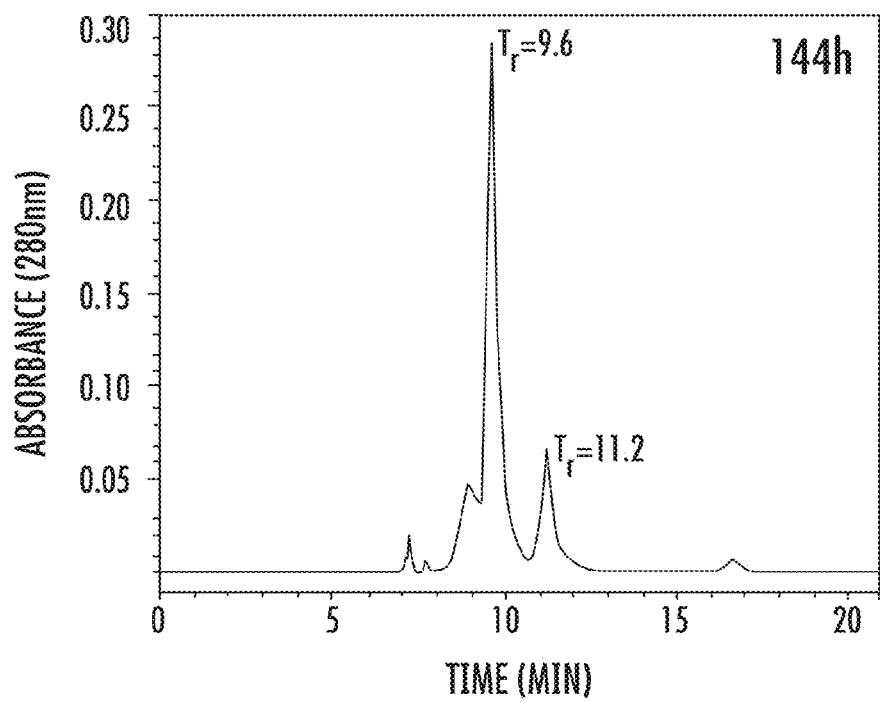
Figure 6E:
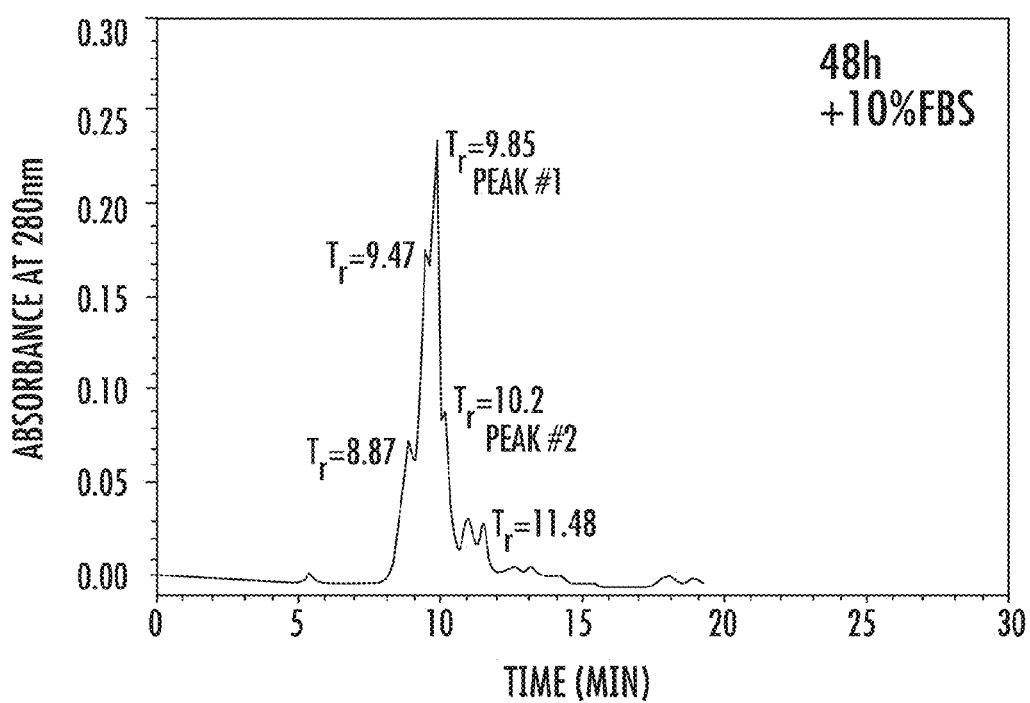

Endogenous metabolites of EPA: To relate the potent anti-leukemic effects of EPA-derived CyPGs to their endogenous production, the cellular biosynthesis of PGD$_3$, $\Delta^{12}$-PGJ$_3$ and 15d-PGJ$_3$ was examined in murine macrophage-like cells (RAW264.7) cultured with EPA (50 μM). RAW264.7 cells, which express H-PGDS[26], were stimulated with bacterial endotoxin lipopolysaccharide (LPS; 50 ng/ml) to induce expression of COX-2. Treated cells produced detectable amounts of PGD$_3$ and its metabolites at 48 h post-LPS treatment. LC-MS analysis of culture media supernatants confirmed the increased production of PGD$_3$, $\Delta^{12}$-PGJ$_3$, and 15d-PGJ$_3$ (FIG. 1A; FIG. 6) only in cells treated with EPA. Based on the LC-retention times and mass fragmentation patterns, the cellular metabolites were identified as PGD$_3$ (m/z 349; FIG. 6A), $\Delta^{12}$-PGJ$_3$ (m/z 331.45; FIG. 1B) and 15d-PGJ$_3$ (m/z 313.45; FIG. 6A). These metabolites were not seen in cells cultured without exogenous EPA (FIG. 1A). It was estimated that treatment of macrophages with 50 μM EPA produced ~0.15 μM of $\Delta^{12}$-PGJ$_3$/10$^6$ cells in 48 h. Non-enzymatic dehydration of PGD$_3$ in phosphate buffered saline produced PGJ$_3$, $\Delta^{12}$-PGJ$_3$, and 15d-PGJ$_3$ in-vitro. Incubation of PGD$_3$ (100 μg/ml; Cayman Chemicals) in a serum free environment for 24-48 h at 37° C. led to the formation of $\Delta^{12}$-PGJ$_3$, PGJ$_3$ ($\Delta^{13}$-PGJ$_3$) (PGJ3 is also called D13-PGJ3 due to the unsaturation at carbon 13; this is a isomer that is formed), and 15d-PGJ$_3$ that were well resolved on a reverse phase LC (C$_{18}$) column with retention times 9.63, 9.97, and 11.02 min, respectively (FIG. 6B, C). Prolonged incubation of PGD$_3$ up to 144 h at 37° C. also produced these metabolites, with $\Delta^{12}$-PGJ$_3$ predominating over the others (FIG. 6C). Presence of serum (10%) did not affect the conversion of PGD$_3$ (FIG. 6E). UV-spectroscopic analysis of the purified $\Delta^{12}$-PGJ$_3$ confirmed the presence of a conjugated diene-like structure with a $\lambda_{max}$ of 242 nm; while PGJ$_3$ and 15d-PGJ$_3$ showed a distinct peak at ~300 nm, which is characteristic of the cyclopentenone structure. Together, these data confirm the endogenous production of PGD$_3$ metabolites and the enhanced stability of $\Delta^{12}$-PGJ$_3$ in an aqueous environment.

Figure 1C:
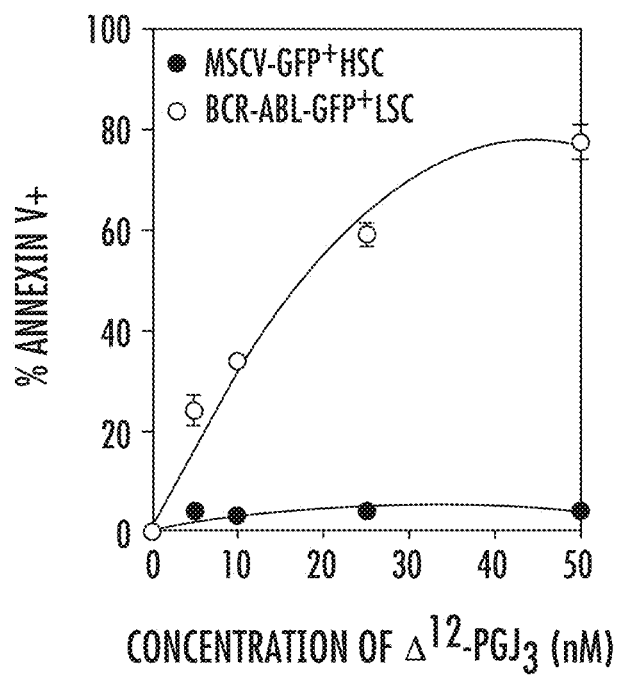
Figure 1D:
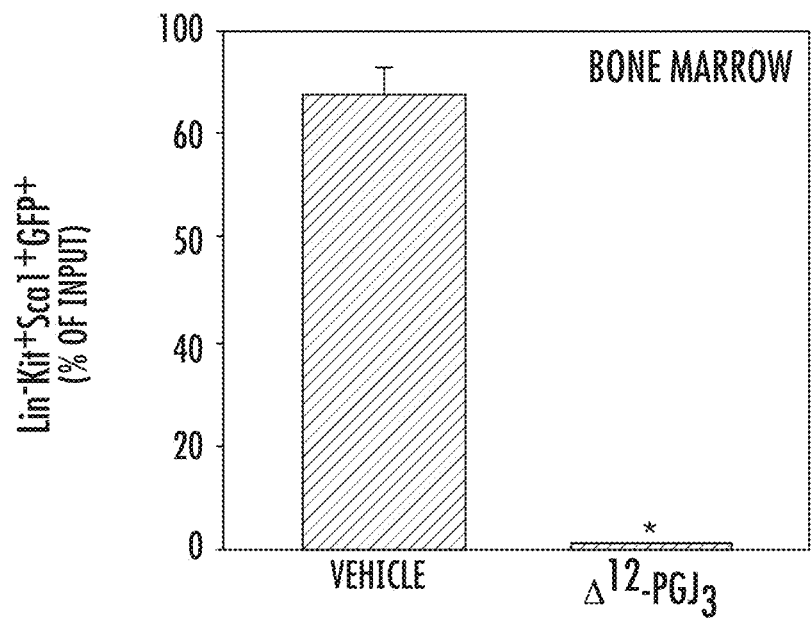
Figure 1E:
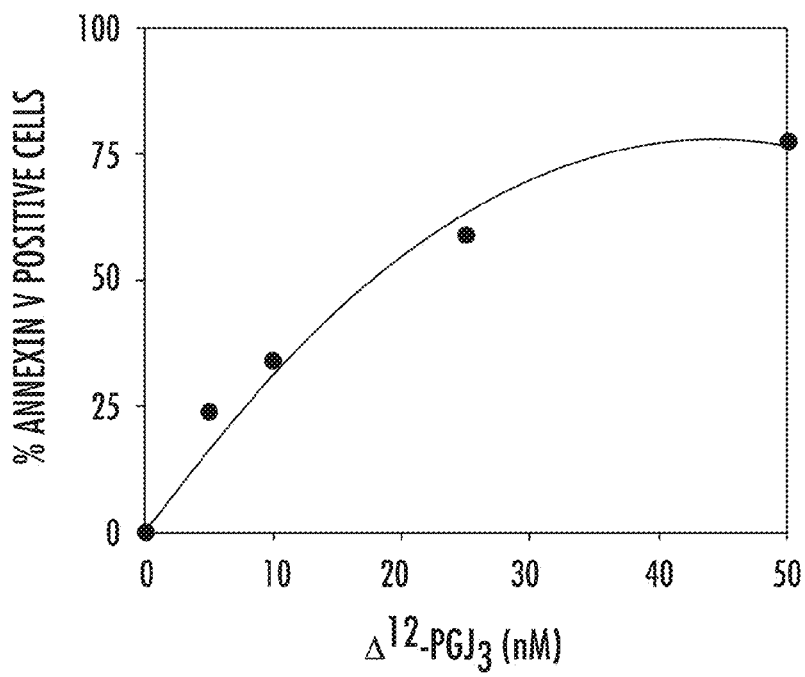
Figure 1F:
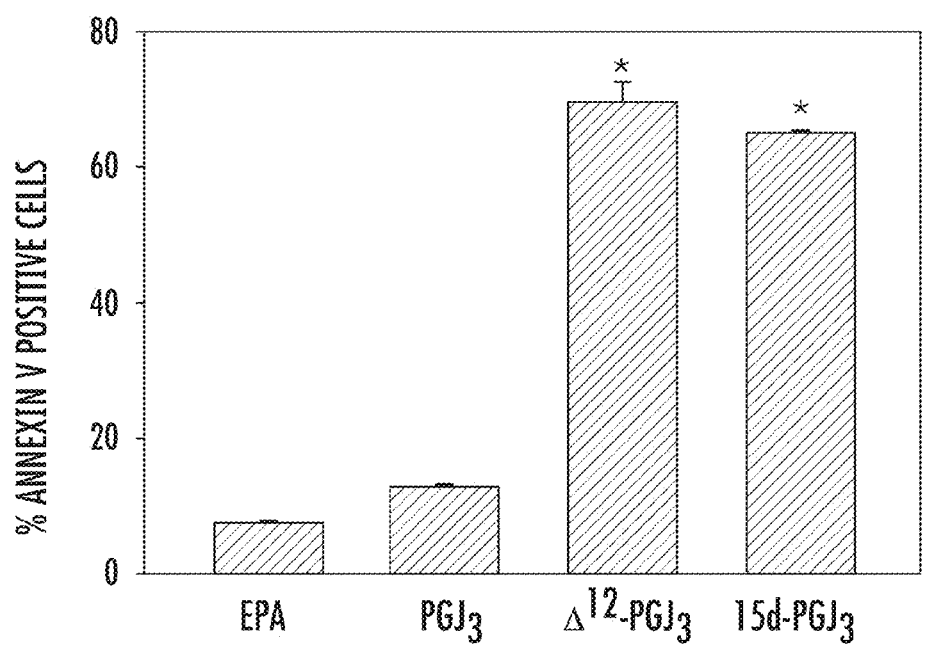
Figure 7A:
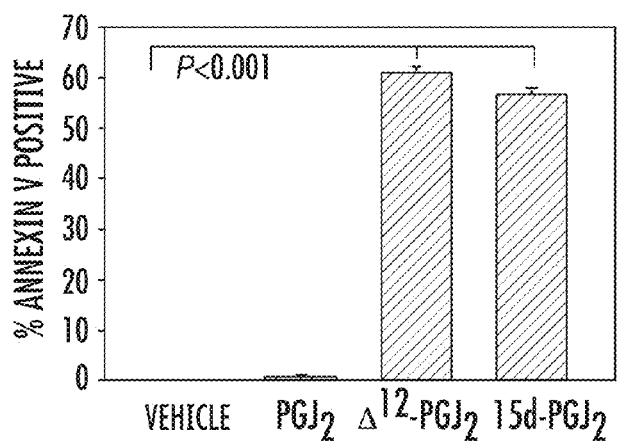
FIG. 7 shows a dose-dependent pro-apoptotic effect of CyPGs on LSCs.
Figure 7B:
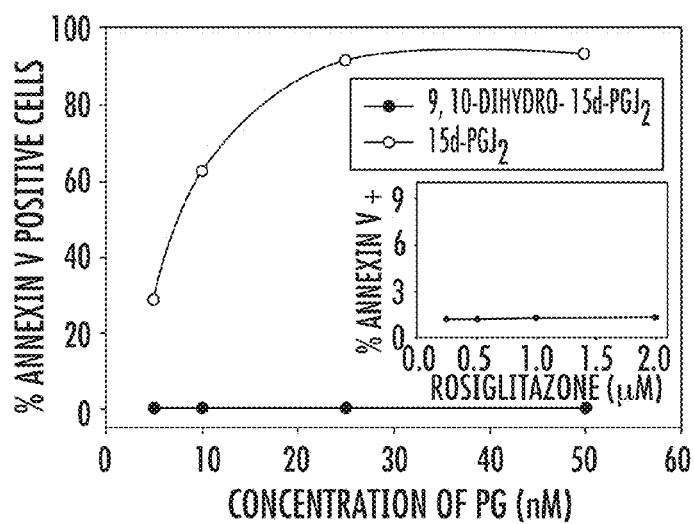
Figure 7C:
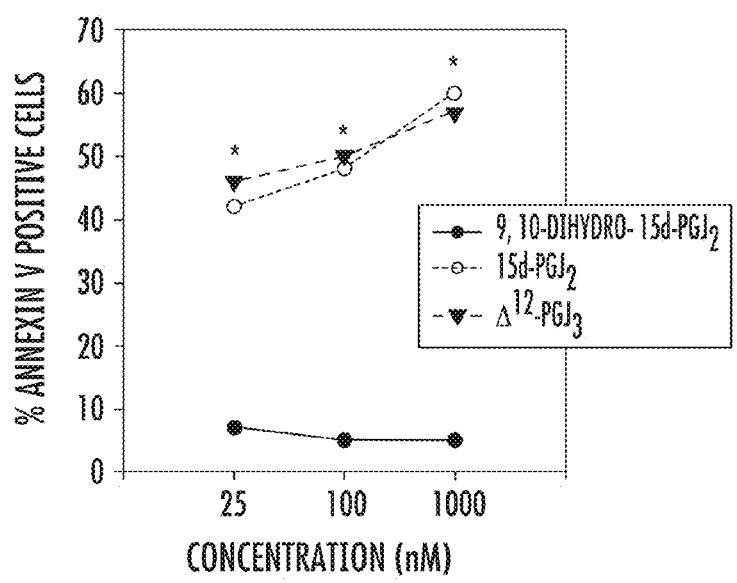

$\Delta^{12}$-PGJ$_3$ induces apoptosis of LSCs: Here, the pro-apoptotic properties of PGD$_3$ metabolites were examined in the two well-studied murine models of leukemia. Mice were transplanted with HSCs transduced with a BCR-ABL expressing retrovirus (hereafter referred to as BCR-ABL mice). Incubation of Kit$^+$Sca1$^+$Lin$^-$GFP$^+$LSCs isolated from the spleen of BCR-ABL mice with low doses of $\Delta^{12}$-PGJ$_3$ significantly increased apoptosis of these cells with an IC$_{50}$ of ~12 nM, but did not affect the normal HSCs, that are represented by Kit$^+$Sca1$^+$Lin$^-$GFP$^+$ cells isolated from mice transplanted with HSCs transduced with a MSCV-GFP control virus (hereafter referred to as MSCV-control mice) (FIG. 1C). Similar effects were also observed when BCR-ABL LSCs (Kit$^+$Sca1$^+$Lin$^-$GFP$^+$) isolated from the bone marrow were treated ex vivo with 012 PGJ$_3$ (A (FIG. 1D). An identical effect was also observed with FV-LSCs (FIG. 1E). Incubation of FV-LSCs with EPA had no effect, while PGJ$_3$ displayed only a 2-fold increase in apoptosis, $\Delta^{12}$-PGJ$_3$ and 15d-PGJ$_3$ treatment at 25 nM led to a significant increase (~75%) in apoptosis (FIG. 1F). The effects of ARA-derived PGJ$_2$, $\Delta^{12}$-PGJ$_2$ and 15d-PGJ$_2$ on FV-LSCs and LSCs derived from BCR-ABL mice were also examined. Responses similar to $\Delta^{12}$-PGJ$_3$ with $\Delta^{12}$-PGJ$_2$ and 15d-PGJ$_2$ were observed, while PGJ$_2$ was largely ineffective (FIG. 7A). In contrast, there was no apoptosis of FV-LSC treated with 9,10-dihydro-15d-PGJ$_2$, a 15d-PGJ$_2$ derivative that lacks an unsaturation at carbon-9 (FIG. 7B). Ex vivo treatment of Sca1$^+$GFP$^+$Kit$^+$ BCR-ABL$^+$LSC sorted from the spleen of transplanted mice with 25-1000 nM of $\Delta^{12}$-PGJ$_3$ or 15d-PGJ$_2$ significantly increased their apoptosis; while 9,10-dihydro-15d-PGJ$_2$ was ineffective even at high concentrations up to 1 μM (FIG. 7C). While all the data described herein clearly demonstrated the proapoptotic ability of $\Delta^{12}$-PGJ$_3$, it was next examined if $\Delta^{12}$-PGJ$_3$ modulated NF-κB or PPARγ, which has been shown to be the mechanism by which 15d-PGJ$_2$ induces apoptosis (Rossi et al., Nature. 2000; 403:103-108; Forman B M et al., Cell. 1995; 83:803-812). $\Delta^{12}$-PGJ$_3$ did not affect the NF-κB pathway as seen by gel shift analysis at concentrations in high nM range in LPS-treated RAW264.7 cells. Furthermore, analysis of the NF-κB activation in sorted BCR-ABL$^+$ LSCs treated with $\Delta^{12}$-PGJ$_3$ by EMSA and Western blotting of nuclear extracts also demonstrated lack of activation of NF-κB. Also, $\Delta^{12}$-PGJ$_3$ was unable to activate PPARγ in reporter assays at nanomolar concentrations that caused apoptosis of LSC. Along the same lines, treatment of FV-LSCs with rosiglitazone, a synthetic agonist of PPARγ (Nolte R T et al., Nature. 1998; 395:137-143) did not affect proliferation of LSC indicating that the apoptotic pathway did not involve PPARγ (FIG. 7B, inset). Taken together, the data indicates that an alkylidenecyclopentenone structure in CyPGs is absolutely essential to effectively induce apoptosis of LSCs from two murine models of leukemia by a mechanism that does not involve PPARγ or NF-κB.

Figure 2A:
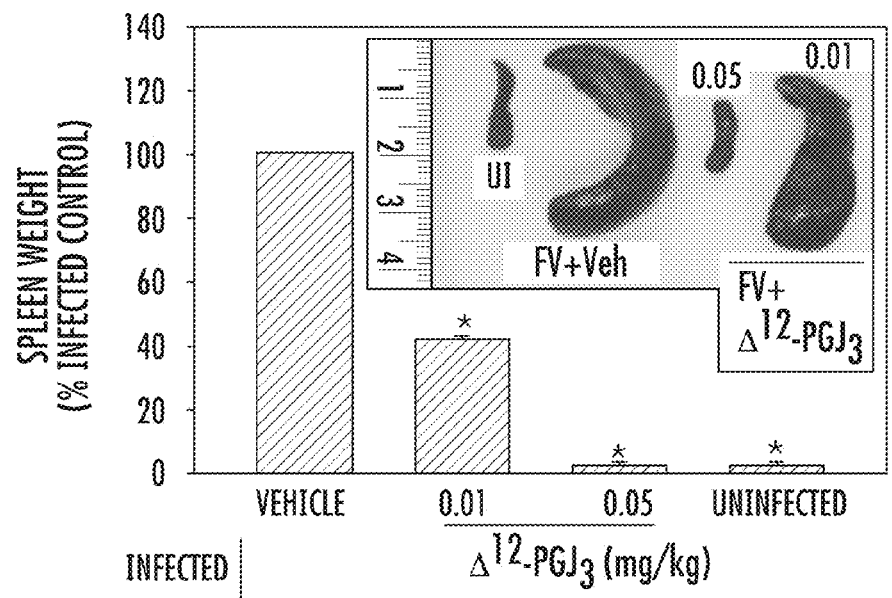
FIG. 2 shows intraperitoneal administration of $\Delta^{12}$-PGJ$_3$ eradicates FV-leukemia in mice. (A) Spleen weight of FV-infected mice treated with various doses of $\Delta^{12}$-PGJ$_3$ (mg/kg body weight). N=10 per treatment group. $\Delta^{12}$-PGJ$_3$ treatment at indicated dosage was started at 1 week post infection for a period of 7 days. *P<0.05. Inset: representative spleens from each treatment group. UI: Uninfected mice. (B) Analysis of LSCs (M34$^+$Kit$^+$Sca1$^+$) in the spleens of FV-infected mice treated with $\Delta^{12}$-PGJ$_3$ or vehicle (Veh) control. (C) CFU-FV colony formation in $\Delta^{12}$-PGJ$_3$ and vehicle control treated mice, *P<0.001. (D) H&E staining of spleen sections from uninfected (left), FV-infected-vehicle treated (middle), and FV-infected-$\Delta^{12}$-PGJ$_3$-treated mice (right) on day 14 post infection. Small box indicated on each section on the left is magnified on the right side. Scale bars, 500 μm.
Figure 2B:
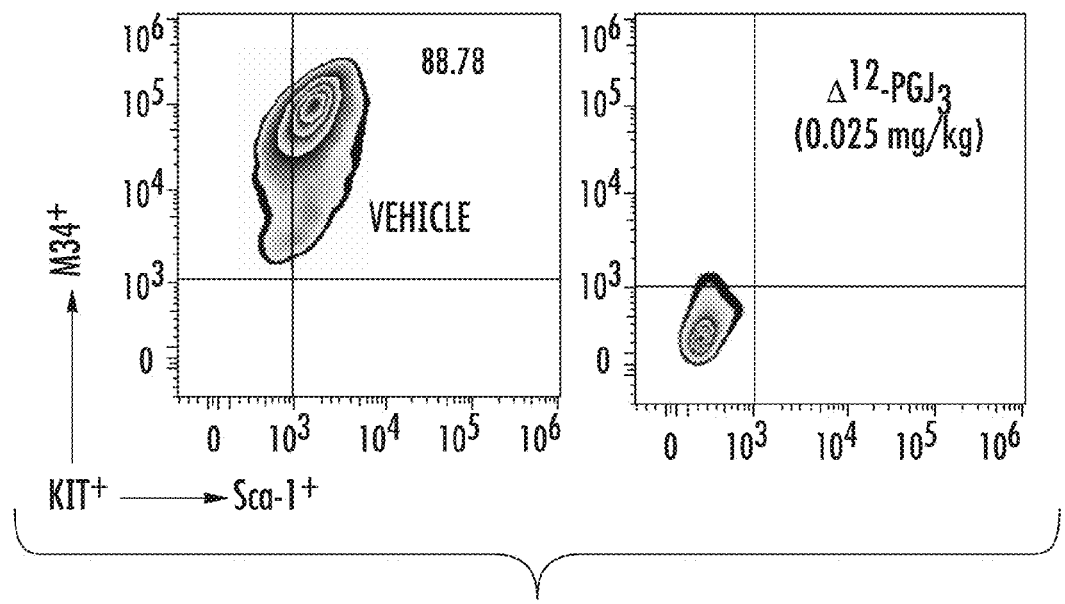
Figure 2C:
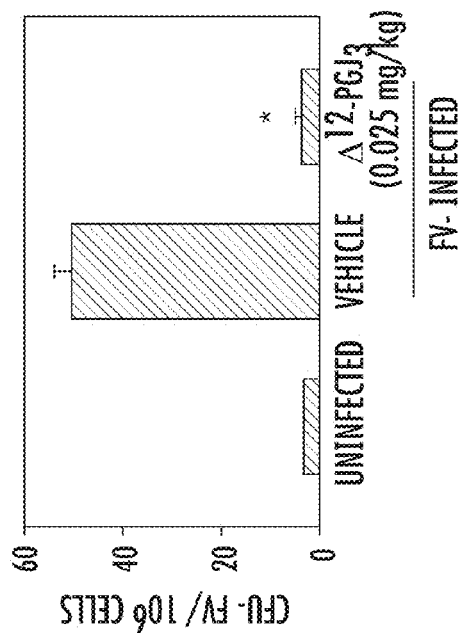
Figure 2D:
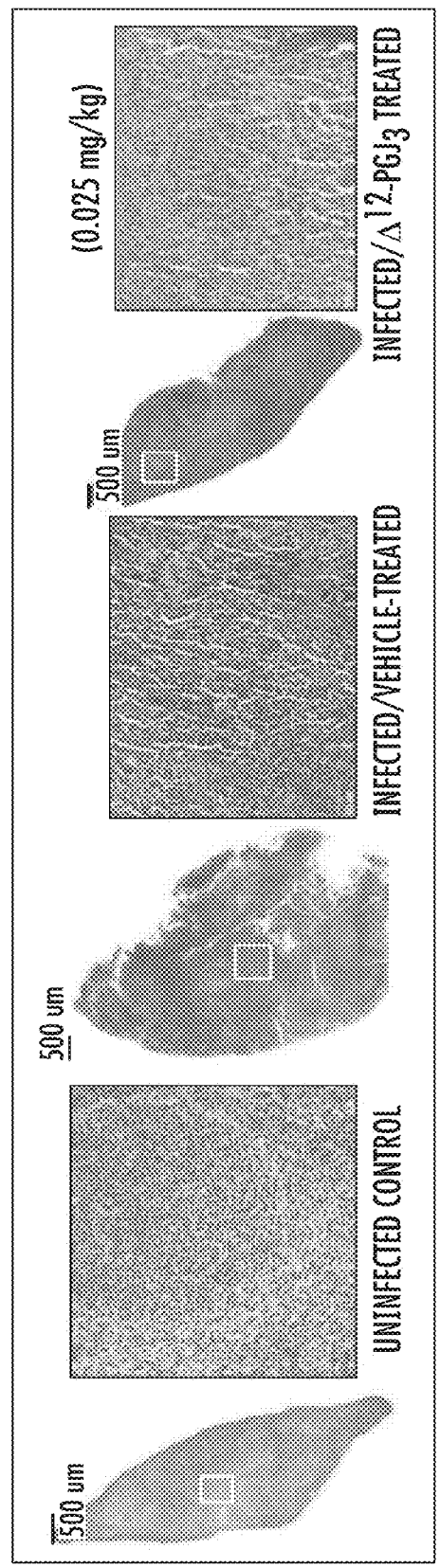

$\Delta^{12}$-PGJ$_3$ eradicates leukemia and alleviates splenomegaly in the FV-infected mice. Given the potent proapoptotic potential of $\Delta^{12}$-PGJ$_3$ on LSC in vitro, the ability of $\Delta^{12}$-PGJ$_3$ to ablate LSCs in FV-infected leukemic mice was tested. Seven days post infection with FV, the mice were treated with $\Delta^{12}$-PGJ$_3$ at 0.01 and 0.05 mg/kg/day for an additional week and the mice were euthanized on day 14-post infection. Compared to the vehicle treated mice, FV-infected mice treated with $\Delta^{12}$-PGJ$_3$ at 0.05 (FIG. 2A) and 0.1 mg/kg showed no signs of splenomegaly. Although 0.01 mg/kg treatment did not completely ablate splenomegaly, there was a significant reduction (~50%) (FIG. 2A). A similar trend was also seen with 15d-PGJ$_2$; while 9,10-dihydro-15d-PGJ$_2$ did not have any effect on the amelioration of splenomegaly. Flow cytometric analysis clearly demonstrated that $\Delta^{12}$-PGJ$_3$ (0.05 mg/kg) completely eradicated the Sca1$^+$Kit$^+$M34$^+$Ter119$^{lo}$ cells in the spleen (FIG. 2B), which represents the LSC population. Identical results were obtained with 15d-PGJ$_2$; while 9,10-dihydro-15d-PGJ$_2$-treatment was ineffective. In agreement with the absence of splenomegaly and complete ablation of LSCs, total leukocyte and reticulocyte counts were decreased to normal levels in $\Delta^{12}$-PGJ$_3$ as well as in 15d-PGJ$_2$-treated mice. Previous work has shown that transformed leukemia cells form colony forming units-Friend virus (CFU-FV) that exhibit factor-independent growth, which can be measured by plating infected spleen cells in methylcellulose media without growth factors (Mager D L et al., Proc Natl Acad Sci USA. 1981; 78:1703-1707). CFU-FV in the $\Delta^{12}$-PGJ$_3$-treated mice was completely reduced to background levels, similar to those in the uninfected mice (FIG. 2C). Histological examination of the vehicle-treated FV-infected spleen showed complete effacement of splenic architecture as a result of infiltration of leukemic blasts, with erythroid progenitor expansion replacing the sinusoids (FIG. 2D). Consistent with the results of decreased splenomegaly, treatment of FV-infected mice with $\Delta^{12}$-PGJ$_3$ led to the better demarcation of peri-arteriolar lymphoid tissue (FIG. 2D). The erythroid progenitor cells were substantially lower and a few giant cells were seen accompanied by an increase in the number of apoptotic bodies with increased individual tumor cell necrosis in the CyPG treated group when compared to the vehicle-treated FV-infected group (FIG. 2D). CyPG treatment of FV-infected mice restored the splenic architecture, with well-defined red and white pulp regions, as in the uninfected mice.

Figure 3A:
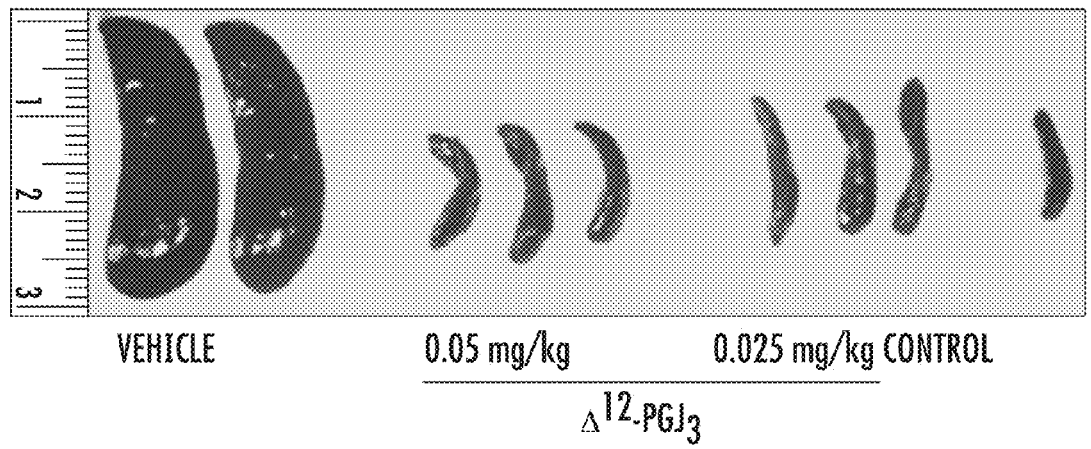
FIG. 3 shows the effect of $\Delta^{12}$-PGJ$_3$ treatment on leukemia induced by transplanting FV-induced LSCs expanded in-vitro into FV-resistant Stk$^{-/-}$ mice. (A) Photograph of spleens from Stk$^{-/-}$ mice seven weeks after transplant with FV-LSCs followed by treatment with vehicle, 0.05 mg/kg, or 0.025 mg/kg $\Delta^{12}$-PGJ$_3$ for 1 week. (B) Spleen weights are shown for the conditions in panel A. N=5 per group, *P<0.05 compared to infected vehicle group. (C) WBC counts in LSC-transplanted Stk$^{-/-}$ mice treated with indicated amounts of $\Delta^{12}$-PGJ$_3$ or vehicle control. N=5 per group, *P<0.05 compared to infected vehicle group. (D) M34$^+$Kit$^+$Sca1$^+$ cells in Stk$^{-/-}$ mice transplanted with LSCs. Spleen cells that were isolated and gated on Kit$^+$, expression of M34 and Sca1 is shown. N=5 per group.
Figure 3B:
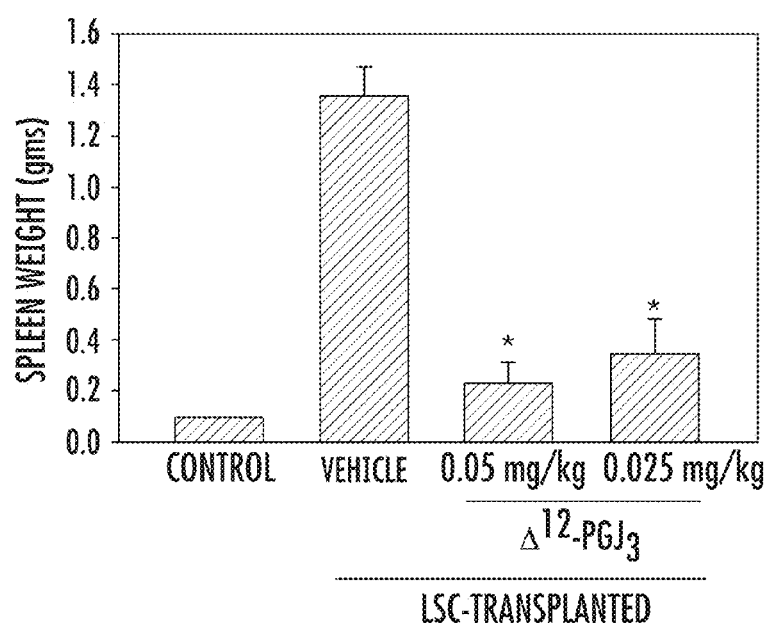
Figure 3C:
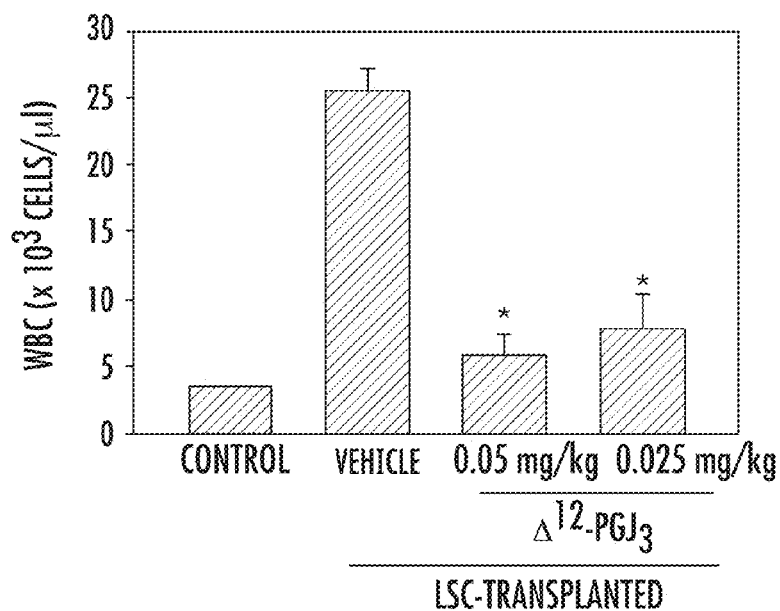
Figure 3D:
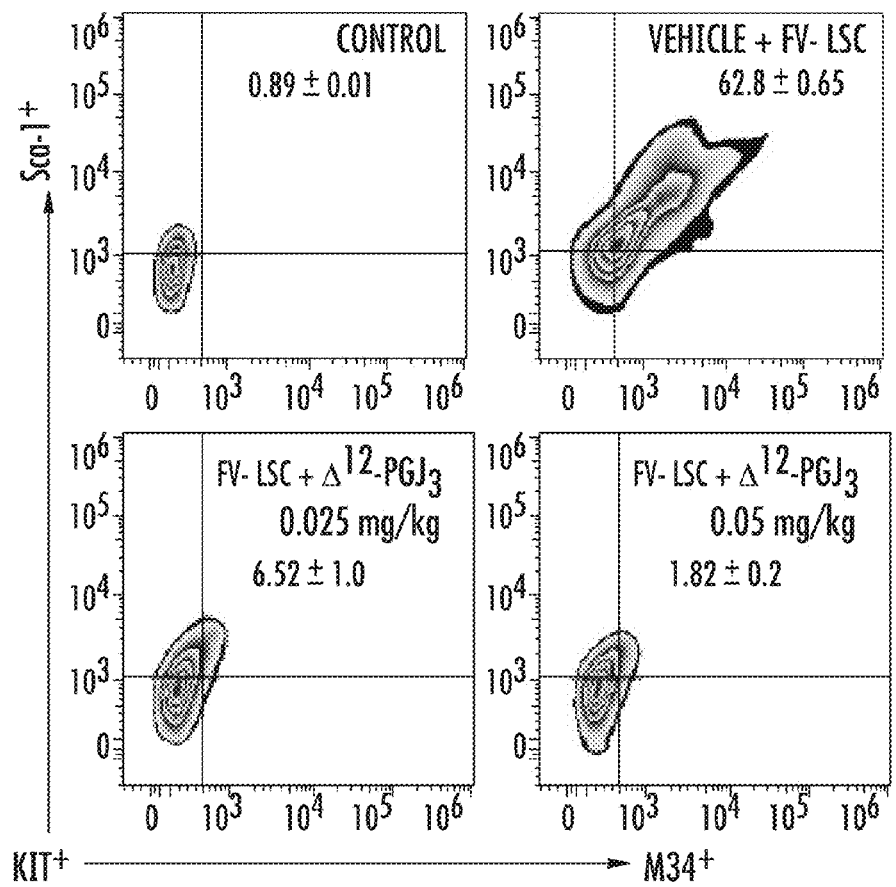

$\Delta^{12}$-PGJ$_3$ inhibits the expansion of LSCs, but not the viral replication. To rule out the possibility that $\Delta^{12}$-PGJ$_3$ blocks FV-induced leukemia by inhibiting viral replication, a second model of FV-induced leukemia was used. Here, the FV-LSCs were transplanted into Stk$^{-/-}$ mice. Short-form Stk (Sf-Stk), a naturally occurring truncated form of Stk/Ron receptor tyrosine kinase, is encoded by the FV-susceptibility locus 2 (Fv2) (Persons D A et al., Nat. Genet. 1999; 23:159-165). Fv2 resistant mice express low levels of Sf-Stk, which fails to support the proliferation of infected cells. Thus, transplantation of FV-LSC into Stk$^{-/-}$ mice results in leukemia caused by the expansion of donor cells and not by the spread of viral infection. LSCs generated from wild type mice were transplanted into syngeneic Stk$^{-/-}$ mice. Treatment with $\Delta^{12}$-PGJ$_3$ (at 0.025 mg/kg and 0.05 mg/kg) led to significantly decreased splenomegaly with a concomitant decrease in leukocyte counts (FIG. 3A-C). Flow cytometric analysis of LSCs in the spleens of transplanted Stk$^{-/-}$ mice indicated complete ablation of M34$^+$Sca1$^+$Kit$^+$cells upon treatment with $\Delta^{12}$-PGJ$_3$ (FIG. 3D); while the LSCs from Stk$^{-/-}$ mice treated with 9,10-dihydro-15d-PGJ$_2$ or the vehicle did not have any effect on their viability nor alleviated splenomegaly. Treatment of FV-induced leukemia with $\Delta^{12}$-PGJ$_3$ or 15d-PGD$_2$ significantly decreased the hematocrit, WBC counts, and reticulocyte counts that are all hallmarks of leukemia; while 9,10-dihydro-15d-PGJ$_2$ had no effect on any parameter tested above (FIG. 3C).

Figure 4A:
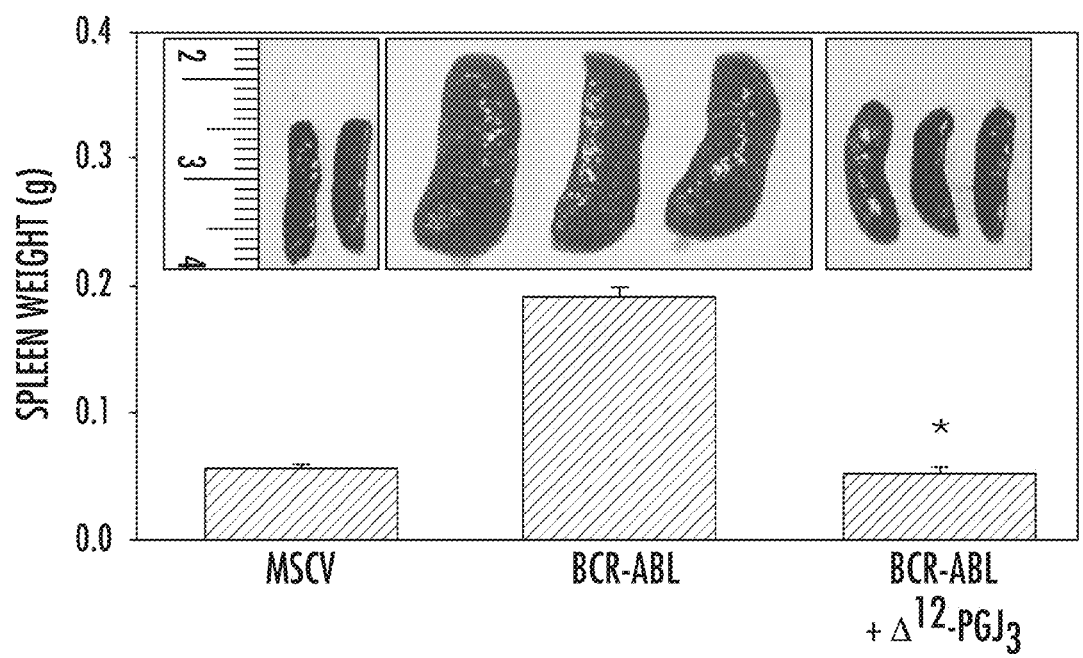
FIG. 4 shows that intraperitoneal administration of $\Delta^{12}$-PGJ$_3$ eradicates LSCs and prolongs survival in a murine CML model. (A) Analysis of the effect of $\Delta^{12}$-PGJ$_3$ treatment on the development of splenomegaly in mice transplanted with BCR-ABL-GFP$^+$LSCs. Representative photographs of spleens from control and BCR-ABL transplanted mice treated with $\Delta^{12}$-PGJ$_3$ (0.025 mg/kg) or vehicle control with corresponding spleen weights. N=10 per treatment group, *P<0.05. (B) Analysis of WBC counts of BCR-ABL$^+$LSC or MSCV-HSC transplanted mice treated with $\Delta^{12}$-PGJ$_3$ or vehicle control. *P<0.0001. (C) Flow cytometric analysis of Sca-1$^+$Kit$^+$GFP$^+$cells in the spleen of mice transplanted with BCR-ABL$^+$LSC or MSCV$^+$HSC treated with $\Delta^{12}$-PGJ$_3$ or vehicle control. N=5 per group; *p<0.001 (D) Analysis of LSCs (Kit$^+$Sca-1$^+$Lin$^-$GFP$^+$) in the bone marrow of BCR-ABL$^+$LSC transplanted and $\Delta^{12}$-PGJ$_3$-treated mice after 5 weeks of last dose of $\Delta^{12}$-PGJ$_3$ (0.025 mg/kg). As a control, BCR-ABL$^+$LSC transplanted mice treated with vehicle for 1 week was used for comparison. (E) Survival curves of mice transplanted with BCR-ABL$^+$LSCs or MSCV-GFP$^+$HSCs upon treatment with $\Delta^{12}$-PGJ$_3$ (0.025 mg/kg) or vehicle. N=8 per treatment group. (F). HSC were isolated from the bone marrow of C57BL/6 mice and plated in methylcellulose (1×10$^6$ cells/ml/well; Epo, SCF, IL-3, and BMP4) with PBS or $\Delta^{12}$-PGJ$_3$ (25 nM) and cultured for a week. Hematopoietic colonies (colony forming cells in culture, CFC) were scored. Data shown is representative of triplicate experiments.
Figure 4B:
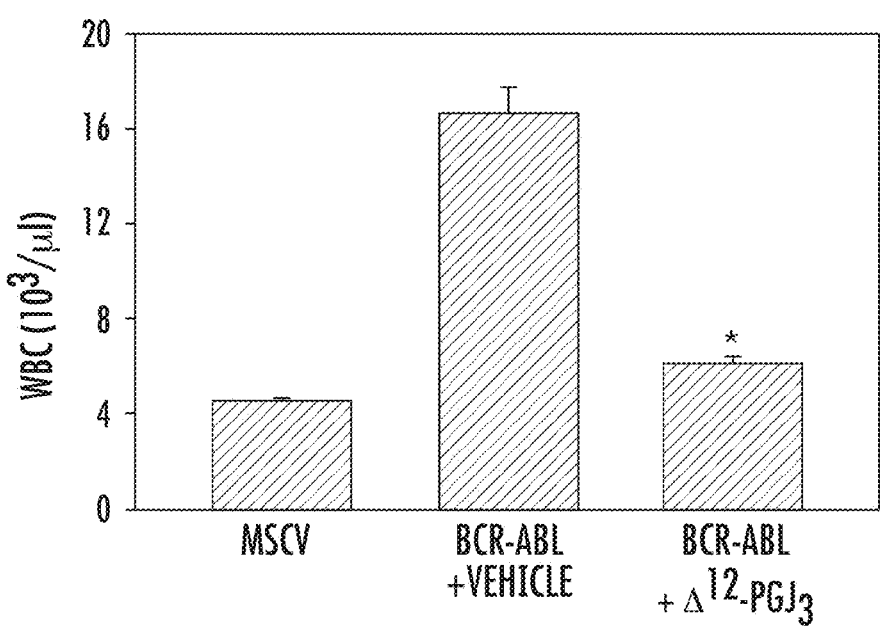
Figure 4C:
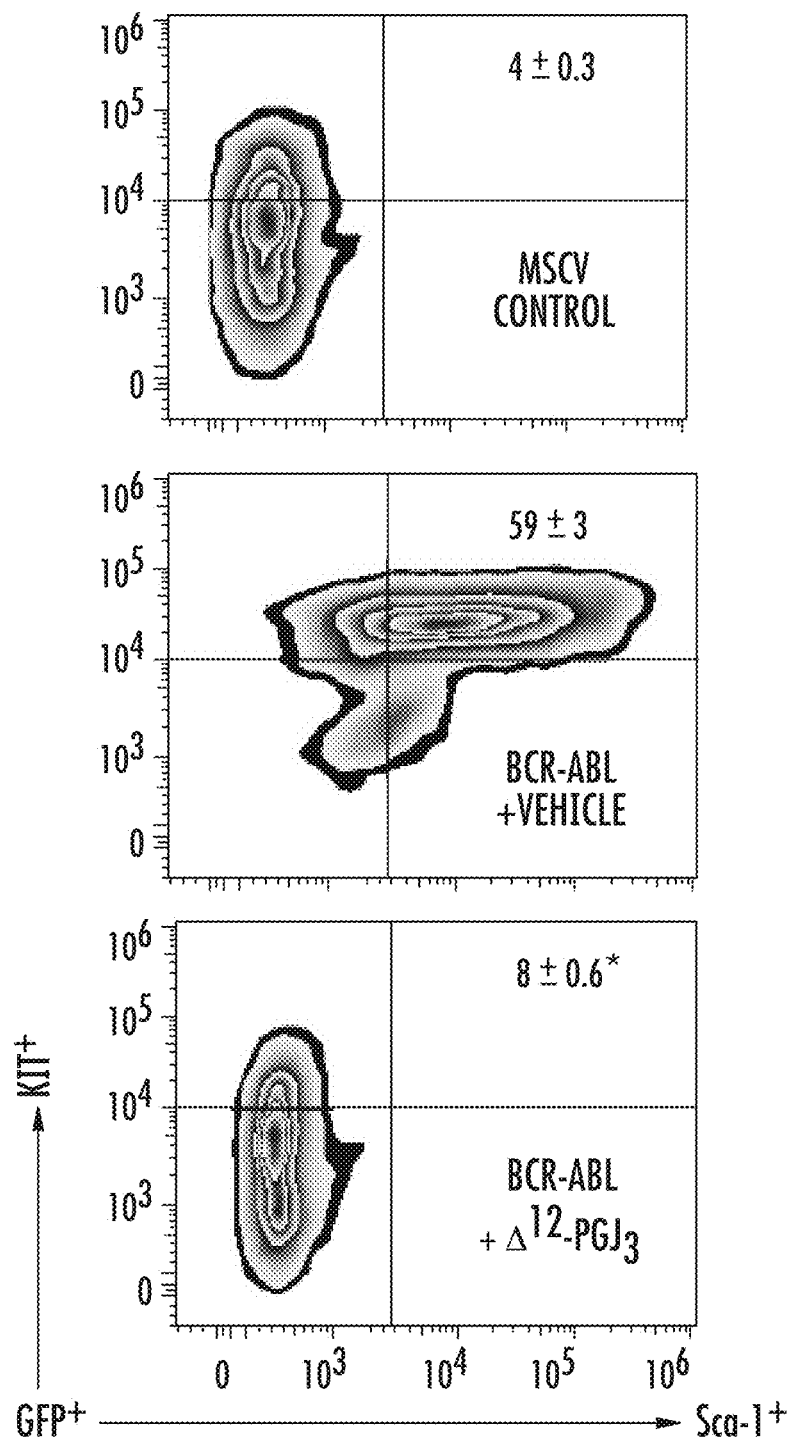
Figure 4D:
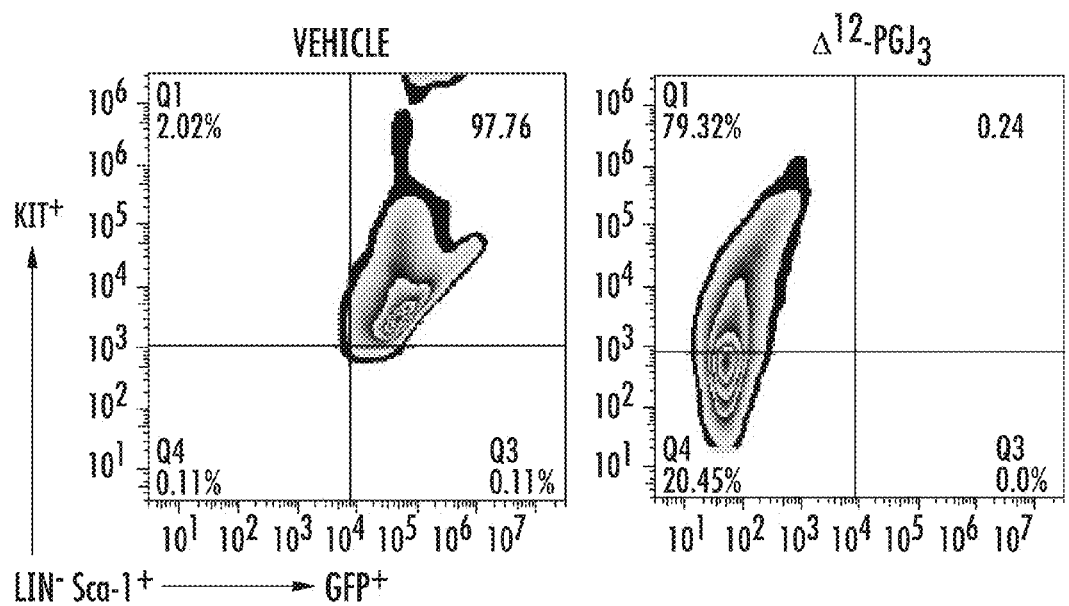
Figure 4F:
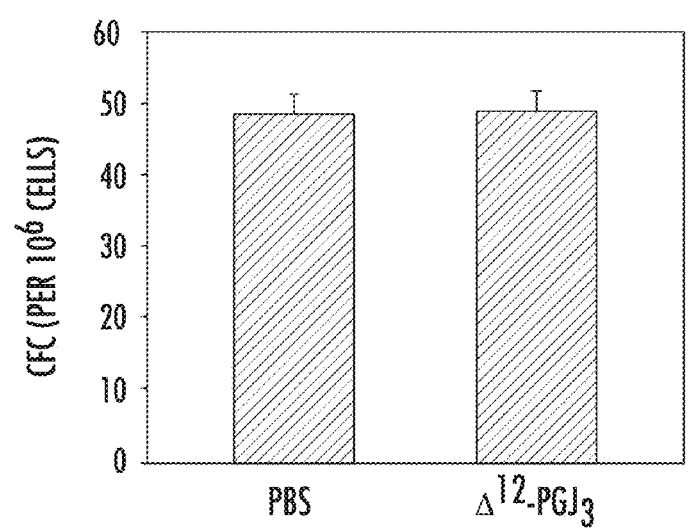
Figure 4E:
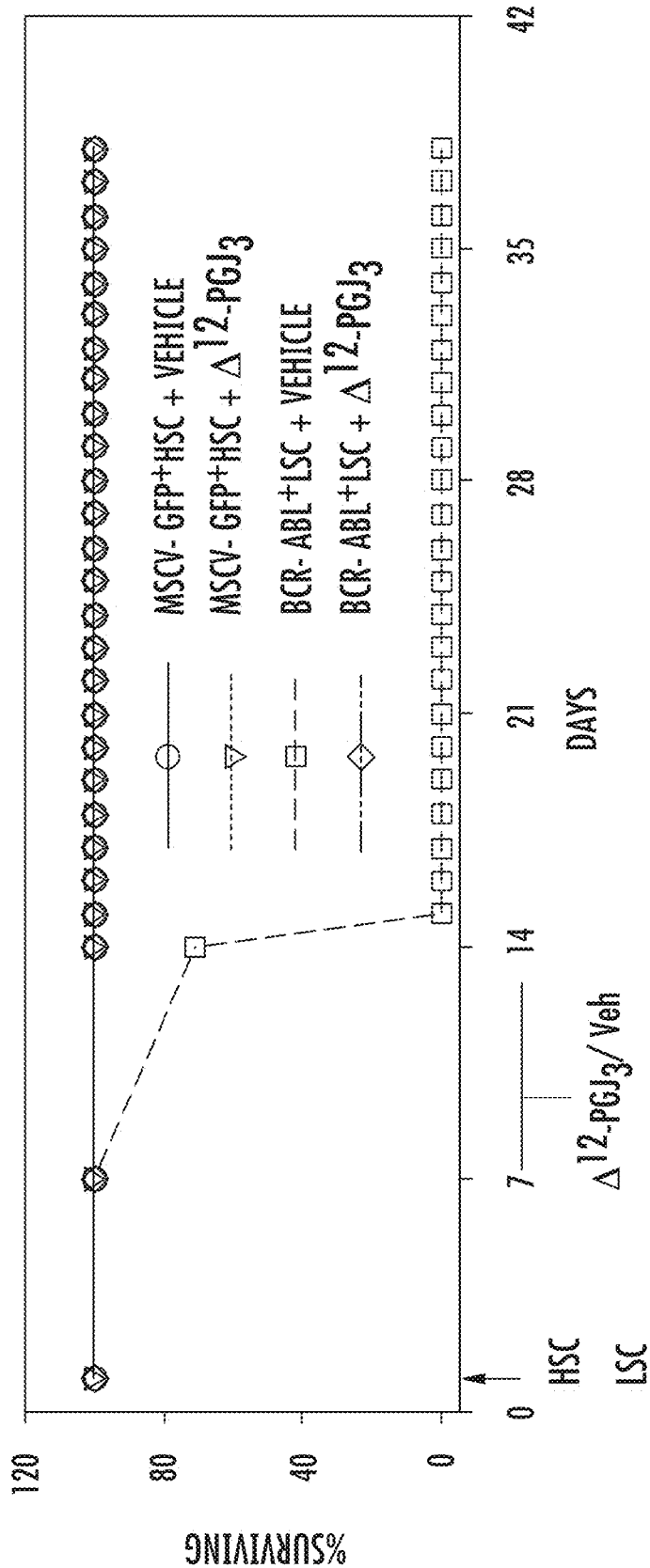

$\Delta^{12}$-PGJ$_3$ alleviates leukemia caused by transplantation of BCR-ABL$^+$LSCs. The in vitro studies of FIG. 1 showed that $\Delta^{12}$-PGJ$_3$ treatment caused apoptosis of BCR-ABL$^+$LSCs, but not the normal HSCs (MSCV-GFP$^+$HSCs). Next, the anti-leukemic activity of $\Delta^{12}$-PGJ$_3$ in BCR-ABL mice, which is a model for the chronic phase of CML (Pear W S et al., Blood. 1998; 92:3780-3792), was examined. As shown in FIG. 4, treatment of mice transplanted with BCR-ABL$^+$LSC with 0.05 mg/kg of $\Delta^{12}$-PGJ$_3$ for 1 week completely alleviated splenomegaly with spleen weights close to those transplanted with the MSCV-GFP$^+$HSCs (FIG. 4A). Furthermore, $\Delta^{12}$-PGJ$_3$ treatment also significantly decreased the leukocyte counts in the peripheral blood (FIG. 4B), decreased Kit$^+$ Sca1$^+$GFP$^+$LSCs in the spleen (FIG. 4C), as well as eradicated Kit$^+$Sca1$^+$ Lin$^-$ GFP$^+$LSCs in the bone marrow of the BCR-ABL$^+$LSC transplanted mice (FIG. 4D). More importantly, treatment of BCR-ABL$^+$LSC transplanted mice with $\Delta^{12}$-PGJ$_3$ rescued all of the mice; while those treated with vehicle died two weeks after transplantation of LSCs (FIG. 4E). In contrast, treatment of mice transplanted with MSCV-GFP$^+$HSC with $\Delta^{12}$-PGJ$_3$ had no effect on WBC counts or other hematological parameters or survival, suggesting that $\Delta^{12}$-PGJ$_3$ does not affect steady state hematopoiesis (FIG. 4E). To further demonstrate that PGJ$_3$ does not affect normal hematopoietic differentiation, it was next tested whether $\Delta^{12}$-PGJ$_3$ treatment had an adverse effect on hematopoietic progenitors by testing its effect on colony forming ability in CFC assays. Bone marrow from 5-FU treated mice was plated in methylcellulose media containing multiple cytokines in the absence or presence of 25 nM of $\Delta^{12}$-PGJ$_3$. There was no difference in the number of CFC in $\Delta^{12}$-PGJ$_3$ treated compared to control (PBS)-treated cells (FIG. 4F).

Figure 5A:
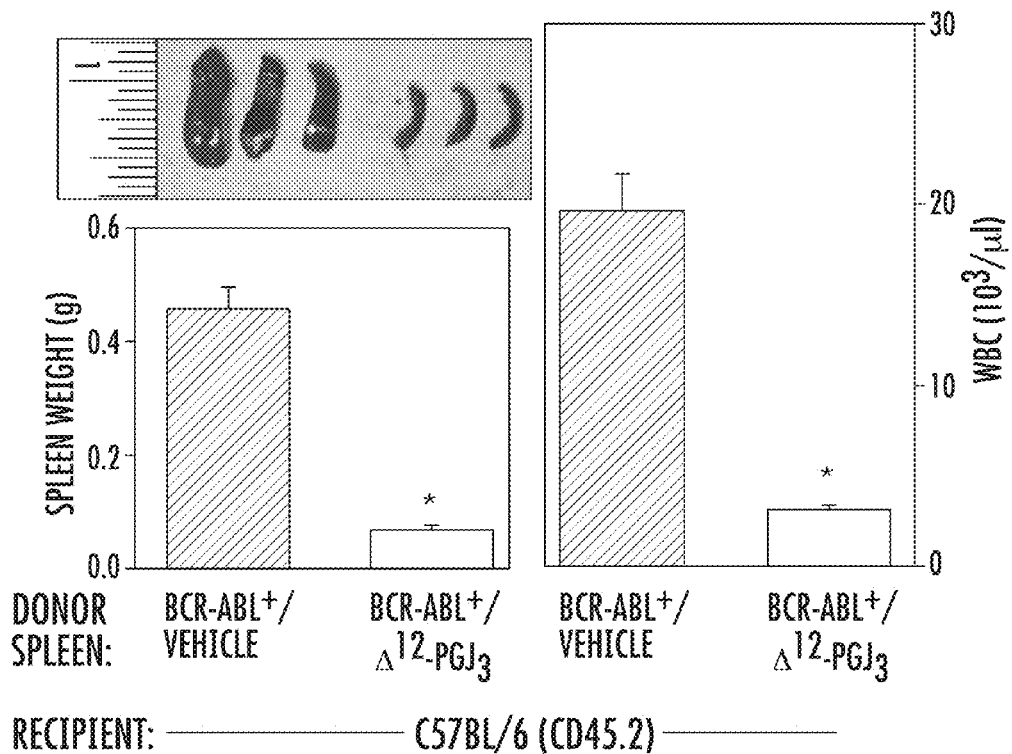
FIG. 5 demonstrates that secondary transplantation of spleen cells from $\Delta^{12}$-PGJ$_3$-treated recipients show absence of leukemia. Panels A-C represent secondary transplantation of CD45.1+BCR-ABL mice treated with $\Delta^{12}$-PGJ$_3$ or vehicle control transplanted into CD45.2 recipient mice. Panels D-E represent FV-LSCs from $\Delta^{12}$-PGJ$_3$ or vehicle control treated mice were transplanted into secondary BALB/c-Stk$^{-/-}$ recipients. (A). Spleen morphology (upper left), spleen weight (lower left) and WBC counts of secondary transplant mice receiving donor cells from vehicle treated or $\Delta^{12}$-PGJ$_3$ treated donor cells (right). (B) Flow cytometry analysis of spleen cells from secondary transplants. Cells were gated on GFP$^+$ and the expression of Kit and Sca1 are shown. (C). Analysis of donor CD45.1 expression in spleen cells. (D) Spleen morphology (upper left), spleen weight (lower left), and WBC counts of secondary transplant mice receiving donor cells from vehicle treated or $\Delta^{12}$-PGJ$_3$ treated donor cells (right). (E) Flow cytometry analysis of spleen cells from secondary transplants. Cells are gated on M34$^+$and the expression of Kit and Sca1 is shown.
Figure 5B:
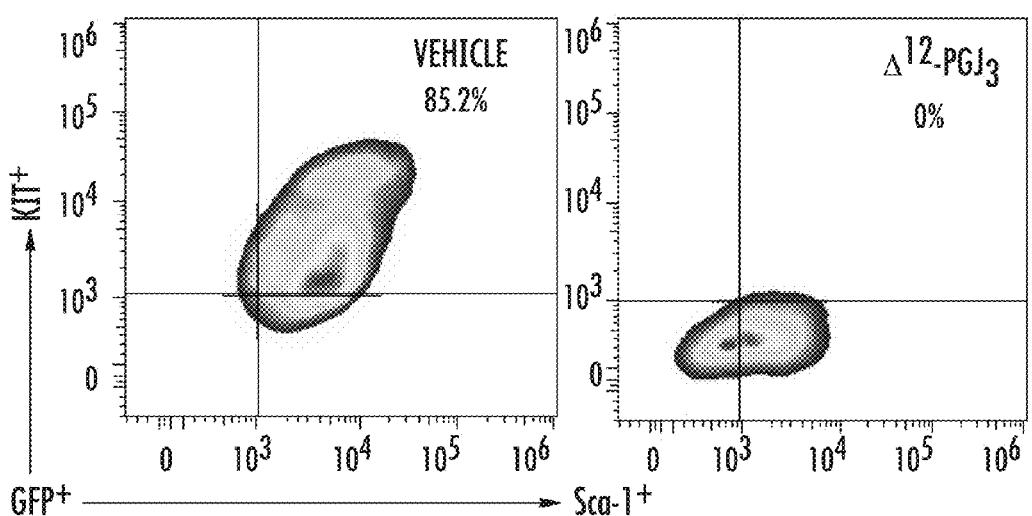
Figure 5C:
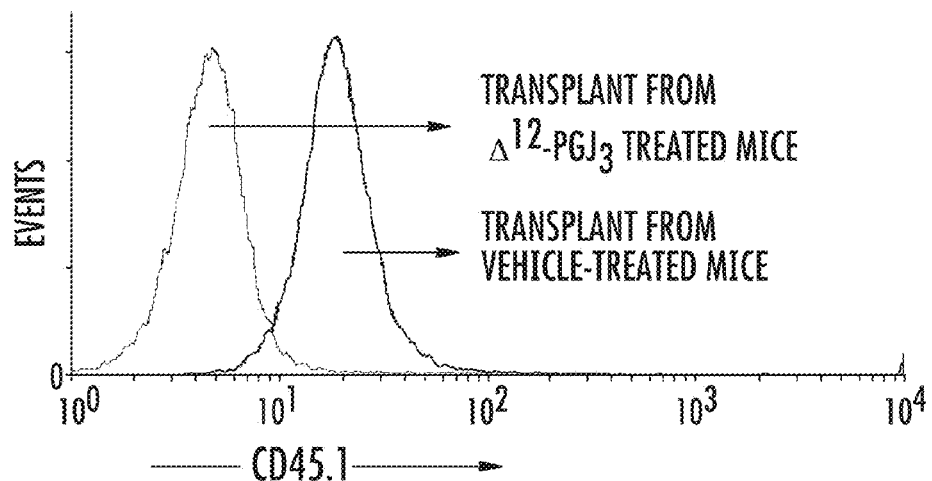
Figure 5D:
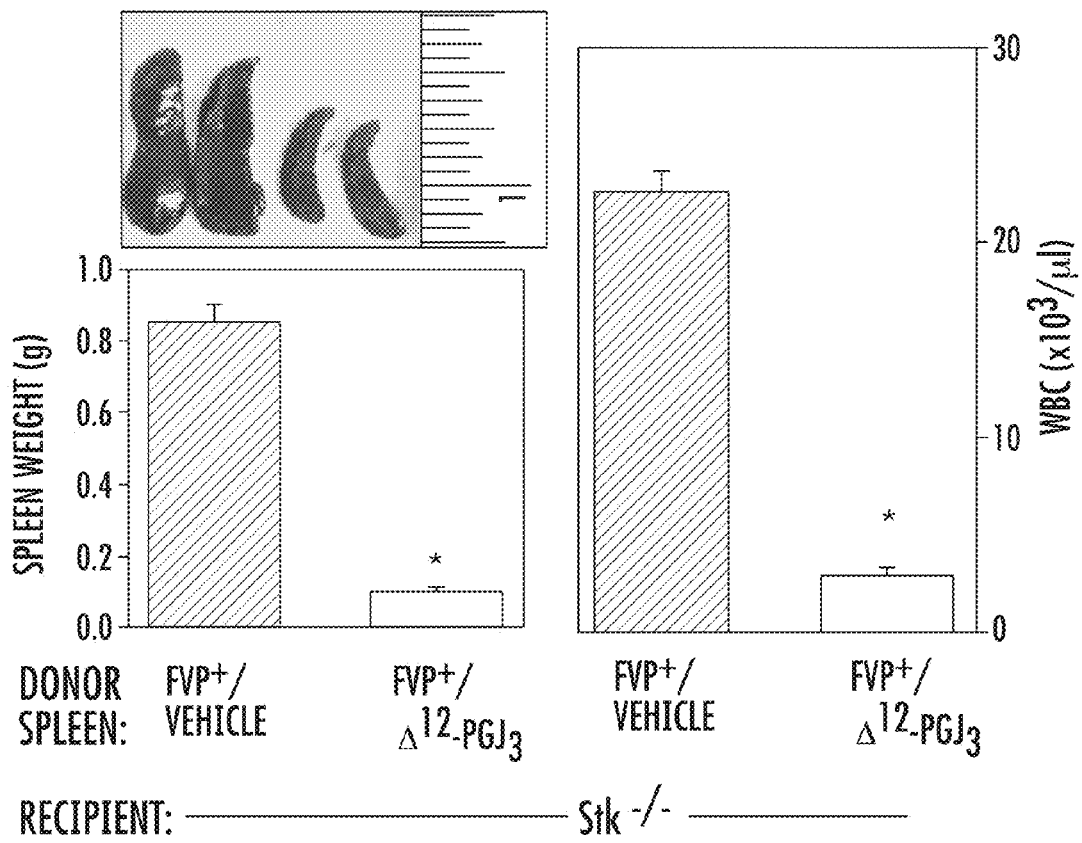
Figure 5E:
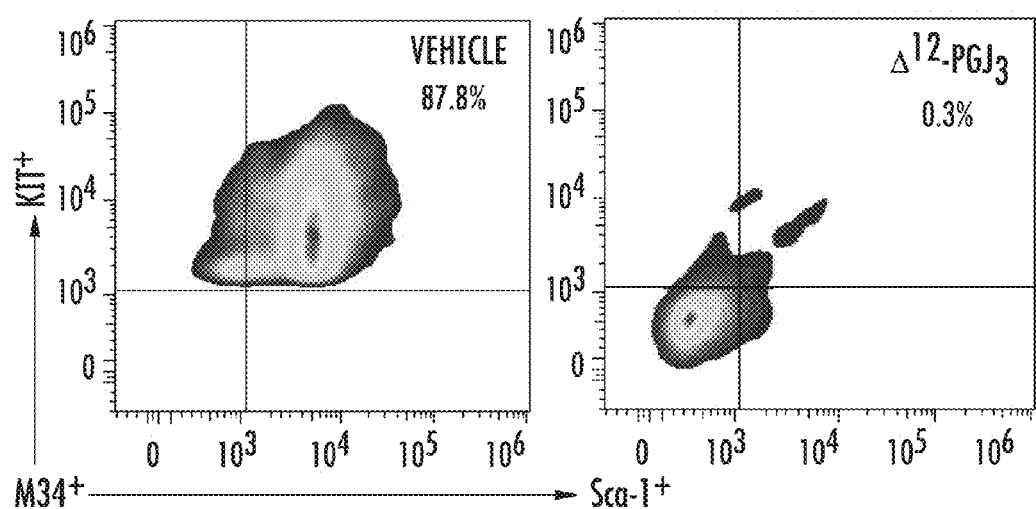

In order to confirm that $\Delta^{12}$-PGJ$_3$ had eradicated LSCs, secondary transplants using splenocytes from $\Delta^{12}$-PGJ$_3$ or vehicle treated BCR-ABL mice were performed. The original donor MIGR-BCR-ABL transduced bone marrow cells were marked with CD45.1$^+$; while the primary and secondary recipients were CD45.2$^+$. Secondary transplants that received donor cells from vehicle-treated mice rapidly developed splenomegaly and high WBC counts indicative of leukemia. In contrast, second recipients of donor cells from $\Delta^{12}$-PGJ$_3$-treated mice failed to develop splenomegaly or high WBC counts (FIG. 5A). Further analysis of spleen for LSCs showed that recipients of donor cells from $\Delta^{12}$-PGJ$_3$-treated mice lacked Kit$^+$Sca1$^+$GFP$^+$ cells. In addition, analysis of CD45.1 expression also showed that CD45.1$^+$ donor cells were not present in the spleen (FIG. 5C). Secondary recipients of donor cells from vehicle-treated mice exhibited large numbers of donor-derived Kit$^+$Sca1$^+$GFP$^+$ and CD45.1$^+$ donor cells in their spleens (FIGS. 5B and C). Similar secondary transplant experiments were performed with donor spleen cells isolated from FV-LSC transplanted BALB/c-Stk$^{-/-}$ mice treated with $\Delta^{12}$-PGJ$_3$ or vehicle. Similar to the BCR-ABL secondary transplants, mice receiving donor cells from $\Delta^{12}$-PGJ$_3$ treated mice failed to develop splenomegaly or high WBC counts and lacked LSCs in their spleens (FIGS. 5D and E). Taken together, these data clearly demonstrate the ability of $\Delta^{12}$-PGJ$_3$ to eradicate LSCs in two diverse murine models of myeloid leukemia.

EPA-metabolites selectively activate p53 in LSC: Ex-vivo treatment of sorted LSCs from FV-infected mice with 10 or 25 nM of $\Delta^{12}$-PGJ$_3$ for 12 h led to significant upregulation of p53 expression at the transcript level. Similarly, treatment of LSCs with 15d-PGJ$_2$ also showed a similar trend; while 9,10-dihydro-15d-PGJ$_2$ was ineffective. Interestingly, PGJ$_2$ treatment upregulated the expression of p53 to only a minor degree, but not to the extent observed with other CyPGs. However, preincubation of PGJ$_2$ with media (at 37° C.) for 42 h prior to addition of LSCs led to increased expression of p53, which suggests a time-dependent isomerization event that possibly converts PGJ$_2$ ($\Delta^{13}$ PGJ$_2$) to $\Delta^{12}$-PGJ$_2$ or 15d-PGJ$_2$ and PGJ$_3$ ($\Delta^{13}$-PGJ$_3$) to $\Delta^{12}$-PGJ$_3$ or 15d-PGJ$_3$ that makes the latter metabolites more potent than the precursor (FIG. 1E). Treatment of BCR-ABL$^+$ LSCs ex vivo with $\Delta^{12}$-PGJ$_3$ or 15d-PGJ$_2$ (25 nM) also led to a similar increase in p53 mRNA; while 9,10-dihydro-15d-PGJ$_2$-treatment was ineffective. Time course analysis showed that p53 transcript levels rapidly increased following treatment of FV-LSCs ex vivo with $\Delta^{12}$-PGJ$_3$ such that by 12 h maximal p53 expression was observed. Analysis of p53 expression in total spleen of uninfected and vehicle-treated FV infected mice clearly showed no increase; however $\Delta^{12}$-PGJ$_3$-treated mice (treated for 1 week) showed a significant expression of p53 in the spleen. Similarly, an increase in the nuclear levels of p53 protein was observed in sorted LSC treated with $\Delta^{12}$-PGJ$_3$ for 12 h, but not in the untreated or vehicle-treated cells. To confirm the role of p53 as a critical mediator of $\Delta^{12}$-PGJ$_3$-dependent LSC apoptosis, the pro-apoptotic role of CyPGs was examined in murine erythroleukemia (MEL) cells that lack functional p53. MEL cells are derived from CFU-FV that has been expanded into a cell line. Treatment of MEL cells with $\Delta^{12}$-PGJ$_3$ failed to initiate apoptosis. MEL cells exhibited sensitivity to treatment with anti-leukemic drugs such as daunorubicin, mitoxantrone, and cytarabine, but not to nutlin, a small molecule inhibitor of MDM2-p53 interaction that causes reactivation of p53. These data confirm the role of $\Delta^{12}$-PGJ$_3$-dependent activation of the p53 pathway in apoptosis of LSCs.

The activation of p53 activity is known to be regulated by an ATM-dependent signaling pathway. It was next examined if ATM played a critical role in the pro-apoptotic activity of $\Delta^{12}$-PGJ$_3$. In addition to increased phosphorylated-p53 protein, an increase in the levels of pChk2 was observed only in the total spleen extracts from the $\Delta^{12}$-PGJ$_3$-treated mice transplanted with FV-LSCs. TUNEL staining of splenic sections from FV-infected mice showed increased apoptosis only in the $\Delta^{12}$-PGJ$_3$-treated group. In agreement with the TUNEL staining results, activation of Bax expression was observed, which is a downstream mediator of apoptosis in the spleens of $\Delta^{12}$-PGJ$_3$-treated FV-infected mice, but not the FV-infected vehicle-treated mice. Taken together, the above experiments suggested the involvement of ATM-p53 signaling axis in promoting $\Delta^{12}$-PGJ$_3$-dependent apoptosis. To further confirm the involvement of ATM, two well characterized inhibitors of ATM were utilized. Preincubation of sorted FV-LSC ex vivo with a high-affinity inhibitor of ATM (MTPO) as well as a dual inhibitor of ATM and the related ATR kinase (CGK-733) followed by treatment with $\Delta^{12}$-PGJ$_3$ blocked the CyPG-dependent expression of p53, which indicated that ATM served as a critical mediator of apoptosis by $\Delta^{12}$-PGJ$_3$. Similar to what was observed with FV, treatment of BCR-ABL$^+$LSCs (Kit$^+$Sca1$^+$Lin$^-$GFP$^+$) with 25 nM of $\Delta^{12}$-PGJ$_3$ led to a significant increase in apoptosis as seen by increased annexin V staining and western blot analysis of caspase 3 and caspase 8 activation. $\Delta^{12}$-PGJ$_3$ treatment led to an increase in p53 transcription; while there was a concomitant decrease in GFP$^+$ cells. Similar to what was observed in FV-LSCs, pretreatment of these cells with MTPO blocked the effect of $\Delta^{12}$-PGJ$_3$ on apoptosis and induction of p53 expression.

DISCUSSION

In the present study, the metabolism of EPA-derived PGD$_3$ to cyclopentenone PGJ$_3$, $\Delta^{12}$-PGJ$_3$, and 15d-PGJ$_3$ in macrophages was demonstrated. Of these stable metabolites that were detected in the macrophage culture media, only $\Delta^{12}$-PGJ$_3$, and 15d-PGJ$_3$ targeted LSCs for apoptosis in FV-induced leukemia and BCR-ABL$^+$ retrovirus-based murine model of CML. In contrast, EPA and PGJ$_3$ were ineffective. These data suggest a structure-function relationship in the form of an alkylidenecyclopentenone structure with an unsaturation at carbon-12 as a requirement for the apoptotic activity of CyPGs.

Based on LC-MS/MS studies, a sufficient quantity of $\Delta^{12}$-PGJ3 (~0.15 μM/10$^6$ macrophages) was produced by macrophages that were well within the concentration required to cause apoptosis of LSCs (IC$_{50}$=7 nM). Despite its pro-apoptotic effects on LSCs, $\Delta^{12}$-PGJ3 had no adverse effects on HSCs or downstream progenitors. These studies indicate that LSCs exhibit increased sensitivity to $\Delta^{12}$-PGJ$_3$ and other related CyPGs in a stereoselective manner. The induction of apoptosis in LSCs by these endogenous metabolites requires the ATM/p53 signaling axis, which causes complete ablation of leukemia in-vivo, as seen in two different mouse models of leukemia. These data show that treatment eliminates LSCs to such an extent that no LSC activity is observed on secondary transplant. These studies support the role of ATM as an important mediator of electrophilic "stress" response pathway in LSCs.

In summary, the ability of macrophages to produce endogenous $\Delta^{12}$-PGJ$_3$ that displays potent proapoptotic activity towards LSCs was demonstrated in two murine models of leukemia by activating the ATM-p53 pathway of apoptosis. Intraperitoneal administration of $\Delta^{12}$-PGJ$_3$ eradicated LSCs in a BCR-ABL retroviral model of CML with no relapse noted five weeks post administration of last dose of $\Delta^{12}$-PGJ$_3$. In contrast, vehicle-treated mice transplanted with LSC failed to survive past day 16 post-transplantation (FIG. 4F). Current anticancer therapies are ineffective against LSCs; thus the ability of a stable endogenous metabolite to ablate LSCs identifies it as a potential therapy. In addition, these results indicate that $\Delta^{12}$-PGJ$_3$, derived from dietary n-3 PUFA, has the potential to serve as a chemopreventive agent in the treatment of leukemia.

Supplementary Information and Methods

Preparation, isolation, and spectroscopic characterization of PGD$_3$ metabolites. PGD$_3$ (Cayman Chemicals) was incubated with 0.1 M sodium phosphate buffer, pH 7.4, containing 0.9% NaCl at a final concentration of 100 µg/ml with shaking at 37° C. for varying periods (24 h-144 h) in sealed brown vials flushed with argon. Similar reactions were performed in the presence of 10% FBS. The reaction mixtures or cell culture media supernatants were acidified with 1 N HCl to pH 3.0 and extracted three times with two volumes of hexane:ethylacetate (50:50). The organic phase was passed over anhydrous sodium sulfate and evaporated under argon. The organic phase was stored in −80° C. until further processing. Eicosanoids were separated by reverse phase LC on a Dynamax semi-quantitative C$_{18}$ column (10×250 mm) using MeCN: H$_2$O: acetic acid (70:30:1) at 2 ml/min and the eluate was monitored at 280 nm. The peaks were collected, concentrated using argon and reconstituted in MS-grade methanol for MS/MS and UV spectroscopic analysis. Eicosanoids were analyzed by direct infusion into a triple quadruple mass spectrometer (API 2000, ABI SCIEX) in the negative electrospray ionization mode. The electrospray voltage and ion spray source temperature were set to −4000 V and 300° C., respectively. Nitrogen was used as curtain (12 psi) and nebulizer (15 psi) gas. The declustering, defocusing, and entrance potentials were set at −50 V, −400 V, and −10 V, respectively.

$\Delta^{12}$-PGJ$_3$ purified by HPLC was used to create a standard calibration curve on the MS operated in multiple reaction-monitoring (MRM) mode for two transitions, 331.5 to 313.5 m/z and 331.5 to 269.5 m/z. UV spectra of all LC-purified PGD$_3$ metabolites in methanol were recorded on a Beckman DU7500 Diode Array Spectrophotometer. The molar extinction coefficients for PGJ$_2$, $\Delta^{12}$-PGJ$_2$, and 15d-PGJ$_2$ (all from Cayman Chemicals) were used to calculate the concentrations of PGJ$_3$, $\Delta^{12}$-PGJ$_3$, and 15d-PGJ$_3$, respectively.

Semiquantitative RT-PCR for p53 and β-actin. Semiquantitative-PCR was performed on the cDNA prepared from LSCs. The bands were visualized on an agarose (1% w/v) gel and evaluated by densitometry.

Apoptosis. The LSCs were diluted in DMEM, resuspended using a 16-gauge needle, and collected by centrifugation. 1×10$^5$ cells were resuspended in 200 µl of binding buffer (0.1 M HEPES with 1.4 M NaCl, 25 mM CaCl$_2$, pH 7.4). Annexin V FITC (BD Biosciences) was incubated with cells for 15 min on ice followed by flow cytometric analysis.

Cell viability studies. MEL cells were cultured in DMEM containing 10% FBS and treated with various commonly used anti-leukemic drugs such as daunorubicin (DNR), mitoxantrone (MIT), and cytarabine (CYT) at a final concentration 1 µM for 24 h. Nutlin (5 µM; Cayman Chemicals), a p53 activator, was used as a control to demonstrate the lack of activation of p53 and apoptosis in the MEL cells. After 24 h of drug treatment, cell proliferation was measured by MTT assay with CCK-8 kit from Dojindo Molecular Technologies, Inc. (Gaithersburg, Md.). All viability values reported are relative to untreated cells (UT) that was designated to be 100%. Results represent the mean±SEM of three independent observations.

Referring to FIG. 6, spontaneous conversion of PGD$_3$ to PGJ$_3$, $\Delta^{12}$-PGJ$_3$, and 15d-PGJ$_3$ in-vitro is shown. FIG. 6a is a schematic showing the pathway of conversion of EPA to CyPGs. Representative MS of PGD$_3$ and 15d-PGJ$_3$ are shown. In FIGS. 6b-d, PGD$_3$ (from Cayman Chemicals) was incubated with 0.1 M sodium phosphate buffer, pH 7.4, containing 0.9% NaCl at a final concentration of 100 µg/ml with shaking at 37° C. for varying periods (24 h-144 h) in sealed brown vials flushed with argon. In FIG. 6e, PGD$_3$ was incubated as above in 10% FBS diluted in phosphate buffered saline for 48 h at 37° C. The PGs were extracted using hexane:ethylacetate (50:50) and the organic phase was concentrated with argon. The eicosanoids were separated by reverse phase LC on a Dynamax semi-quantitative C$_{18}$ column (10×250 mm) using MeCN: H$_2$O: acetic acid (70:30:1) at 2 ml/min and the eluate was monitored at 280 nm. The peaks were collected, concentrated using argon and reconstituted in MS-grade methanol for UV-MS/MS analyses. Representative of N=8 independent reactions.

A UV-Spectroscopic analysis of $\Delta^{12}$-PGJ$_3$ and 15d-PGJ$_3$ as a function of time during conversion was performed. LC-purified $\Delta^{12}$-PGJ$_3$ and 15d-PGJ$_3$ were reconstituted in methanol and analyzed by UV spectroscopy for spectral properties on a Beckman DU7500 Diode Array Spectrophotometer against appropriate solvent background controls. The molar extinction coefficients for PGJ$_2$, $\Delta^{12}$-PGJ$_2$, and 15d-PGJ$_2$ were used to calculate the concentrations of PGJ$_3$, $\Delta^{12}$-PGJ$_3$, and 15d-PGJ$_3$, respectively. Representative of N=3. The results indicate the formation of an alkylidenecyclopentenone structure followed by a intramolecular rearrangement to form $\Delta^{12}$-PGJ$_3$ and the double dehydration product 15d-PGJ$_3$ from PGD$_3$ precursor.

Referring to FIG. 7, a dose-dependent pro-apoptotic effect of CyPGs on LSCs is shown. The ability of CyPGs derived from arachidonic acid (2 series PGs) to induce apoptosis was tested in cultures of LSCs from FV infected mice and in the murine CML model. In FIG. 7A, $\Delta^{12}$-PGJ$_{J2}$, or 15d-PG$_{J2}$ are able to induce apoptosis, compared to vehicle, but PG$_{J2}$ was not.

15d-PG$_{J2}$ is known as a PPAPγ agonist. In FIG. 7B, FV LSCs are treated with 15d-PG$_{J2}$, an inactive form, 9,10-dihydro-15d-PG$_{J2}$ or Rosiglizone, a commercially available synthetic PPAPγ agonist (inset of FIG. 7B). Rosiglizone and 9,10-dihydro-15d-PG$_{J2}$ fail to induce apoptosis. In FIG. 7C $\Delta^{12}$-PG$_B$, 15d-PG$_{J2}$ or 9,10-dihydro-15d-PG$_{J2}$ are tested for their ability to induce apoptosis in a murine CML model. Only $\Delta^{12}$-PG$_{J2}$, 15d-PG$_{J2}$ are active, while 9,10-dihydro-15d-PG$_{J2}$ had no effect. These data show that activation of PPAPγ is not the mechanism by which CyPGs induce apoptosis. In FIG. 7a, Spleen cells from FV-infected mice were sorted for M3$^{4+}$Sca$^{1+}$Ki$^{r+}$ LSCs and incubated with 25 nM of PG$_{J2}$, $\Delta^{12}$-PG$_{J2}$, or 15d-PG$_{J2}$ for 36 h in a methylcellulose stem cell media with 200 ng/ml sonic hedgehog (sHH), 50 ng/ml SCF, and 15 ng/ml BMP4. The cells were stained with annexin V-FITC and analyzed by flow cytometry. Representative of N=4. Means±s.e.m. *P<0.001 compared to vehicle (PBS). In FIG. 7b, a comparison of the proapoptotic function of 9,10-dihydro-15d-PG$_{J2}$ with 15d-PG$_{J2}$ is shown. Inset: Effect of rosiglitazone on the apoptosis of LSC. Rosiglitazone (0.1-2.01 μM) was incubated with LSC in the culture media for 36 h as described earlier and the cells were subjected to annexin-V staining followed by flow cytometry. FIG. 7c shows results from an analysis of apoptosis of BCR-AB$^{L+}$ Ki$^{+}$Sca$^{1+}$ cells isolated from the spleens of mice transplanted with BCR-AB$^{L+}$ transduced HSCs after treatment with CyPGs. LSC were treated ex vivo with indicated concentrations of each compound for 36 h. Mean±s.e.m. shown *P<0.001.

The effect of $\Delta^{12}$-PG$_{J3}$ on NF-κB and PPAPγ was examined. RAW264.7 macrophages were pretreated with DMSO, $\Delta^{12}$-PG$_{J3}$ at 0.25, or 1.0 μM and subsequently stimulated with 100 ng/mL E. coli LPS for 4 h. The nuclear extracts were prepared and the binding of NΦκB to a $^{32}$P-labeled consensus double stranded oligonucleotide probe was examined using gel shift analysis. NS=non-specific band. Lanes 1-5 represent untreated, LPS alone, DMSO+LPS, $\Delta^{12}$PG$_{J3}$ (0.25 μM) +LPS, and $\Delta^{12}$-PG$_{J3}$ (1 μM) +LPS, respectively. BCR-ABL LSCs were sorted from spleens, plated, and treated with PBS, 25 nM $\Delta^{12}$-PG$_{J3}$, or 9,10-dihydro 15d-PG$_{J2}$ for 0, 2 or 6 h. The cells were harvested and nuclear extracts were prepared using standard techniques. Ten μg of nuclear protein was used from each sample for the gel-shift reaction. As a positive control for NF-κB, nuclear extract from LPS-treated murine (RAW264.7) macrophages was used. Anti-p50 Ab was used with this positive control for a supershift, and excess 'cold' probe was used with the positive control as a 'cold competitor'. A Western blot analysis was performed of the above-mentioned nuclear extracts from BCR-ABL LSCs treated with PBS, $\Delta^{12}$-PG$_{J3}$ or 9,10-dihydro-15d-PG$_{J2}$ for various time periods (0-6 h) probed with anti-p65 and anti-β-actin antibodies. In a reporter assay for PPAPγ activation, HEK293T cells expressing ligand-binding domain of human PPAPγ fused to yeast GAL4 DNA binding domain were transfected with a pGalRE-Luc reporter gene. These studies were performed to address the ability of $\Delta^{12}$-PG$_{J3}$ to activate PPAPγ using this well characterized reporter system. Our studies demonstrated that $\Delta^{12}$-PG$_{J3}$ was unable to activate the PPAPγ at concentrations 0.01 μM to 1.0 μM, unlike rosiglitazole that was used as a positive control.

Treatment of mice transplanted with FV LSCs with $\Delta^{12}$-PGJ$_3$ (0.05 mg/kg) does not adversely affect hematological parameters in the mice. Complete blood counts of mice treated with $\Delta^{12}$-PGJ$_3$ (0.05 mg/kg) were examined. There is no difference in treated mice and untransplanted control mice in terms of white blood cell counts, red blood cell counts or platelet counts. Changes in hematological parameters in FV-infected mice upon treatment with CyPGs were examined. FV-infected Balb/c mice were treated with $\Delta^{12}$-PGJ$_3$ (0.05 mg/kg) intraperitoneally for 7 d following which the mice were sacrificed and hematological parameters were analyzed on an Advia blood analyzer. FV-infected $\Delta^{12}$-PGJ$_3$ treated mice were compared to infected vehicle controls. N=5 per group, all data are means±s.e.m. *P<0.05.3% w/v hydroxypropyl-β-cyclodextrin was used as a vehicle in in vivo experiments. Spleen sizes of FV-infected mice that were treated with either vehicle, 9,10-dihydro-15d-PGJ$_2$ (0.05 mg/kg), or 15d-PGJ$_2$ (0.05 mg/kg) were examined; N=3 pre group. Hematological parameters of Balb/c uninfected, infected, and 15d-PGJ$_2$ treated mice were examined. N=5 per group. All data were means±s.e.m. *P<0.05.

15d-PGJ$_2$ was shown to eradicate FV-LSC. FV-LSC were targeted by 15d-PGJ$_2$ in the spleen of FV-infected mice. FV-infected mice were treated with 15d-PGJ$_2$ or 9,10-dihydro-15d-PGJ$_2$ at 0.05 mg/kg for 7 d. The splenic LSC (M34$^+$Sca1$^+$Kit$^+$) cells were analyzed by flow cytometry on day 14 post infection. Treatment with 15d-PGJ2 leads to a significant decrease in LSC numbers as measured by flow cytometry. In addition, 15dPGJ2 significantly decreased the number of transformed leukemia cells that are capable of forming transformed CFU-Friend virus colonies. 15d-PGJ2 does not affect Friend virus viral replication, so in these experiments a single course of treatment with 15dPGJ2 does not eliminate LSCs, which are regenerated by ongoing viral infection. Uninfected and infected vehicle controls were used for comparison. N=3; *P<0.05. Splenocytes from infected mice were treated with vehicle, 9,10-dihydro-15d-PGJ$_2$, and 15d-PGJ$_2$, and were plated in methylcellulose media containing FCS without growth factors to examine if treatment of mice with 15d-PGJ$_2$ or 9,10-drihydro-15d-PGJ$_2$ affected the formation of CFU-FV colonies, which exhibit factor-independent growth. The colonies were counted 10-14 days after plating. N=3 mice per group, *p<0.05.

In order to address the ability of 15d-PGD$_2$ to eradicate FV LSCs in a system where viral infection cannot regenerate LSCs Stk$^{-/-}$ mice were transplanted with in vitro expanded FV-LSCs. Stk$^{-/-}$ mice are resistant to Friend virus infection so the leukemia developed by the transplanted mice is result of the transplanted LSCs and not FV infection. Mice treated with 15dPGJ2 led to the eradication of FV LSCs in the spleen and resolution of the diseases. LSCs sorted from the spleens of FV-infected mice were transplanted into Stk$^{-/-}$ mice (on a Balb/c background). After 6 weeks such mice were treated daily for 1 week with vehicle (hydroxypropyl-β-cyclodextrin), 15d-PGJ$_2$ (0.05 mg/kg), or 9,10-dihydro-15d-PGJ$_2$ (0.05 mg/kg) by intraperitoneal injection. The mice were sacrificed 51 days post LSC transplantation for analysis. An analysis of spleens of mice comparing splenomegaly in vehicle, 15d-PGJ$_2$, or 9,10-dihydro-15d-PGJ$_2$ treated transplanted mice was performed. Spleen weight compared to control (untransplanted mice) after treatment and WBC counts in the peripheral blood of the mice after treatment were examined, and a flow cytometric analysis of the spleen of untransplanted and LSC transplanted mice after treatment was performed. All data were mean±s.e.m. *p<0.05 compared to control or 9,10-dihydro-15d-PGJ$_2$ treated groups. N=5 per group.

$\Delta^{12}$-PGJ$_3$ cannot induce apoptosis in MEL cells because MEL cells have a mutation in the p53 gene. In order to address whether MEL cells are resistant in general to chemotherapy agents, we tested whether MEL cells can be killed by apoptosis when treated with standard anti-leukemia drugs. Treatment with various commonly used anti-leukemic drugs such as daunorubicin (DNR), mitoxantrone (MIT), and cytarabine (CYT) at a final concentration 1 μM for 24 h. Nutlin (5 μM), a p53 activator, was used as a control to demonstrate the lack of activation of p53 and apoptosis in the MEL cells. After 24 h of drug treatment, cell proliferation was measured by MTT assay with CCK-8 kit from Dojindo Molecular Technologies, Inc. (Gaithersburg, Md.). All compounds with the exception of nutlin caused significant apoptosis. The results represent the mean±SEM of three independent observations.

Example 2

Targeting LSCs Via Molecules that Activate DP

Figure 8:
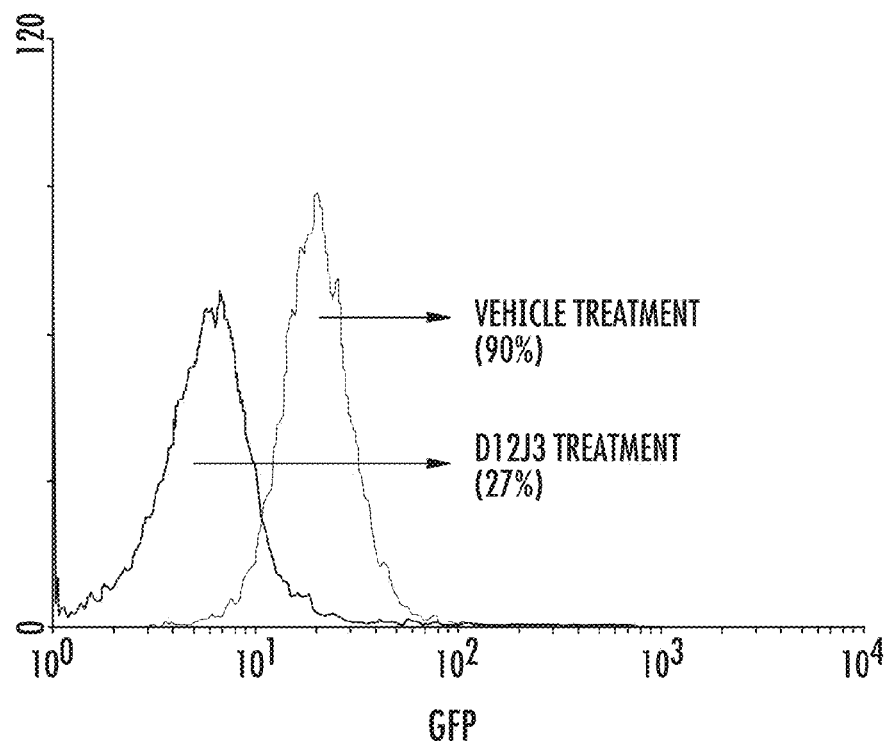
FIG. 8 is a graph showing that imatinib-resistant BCR-ABL(GFP)+ cells are targeted by $\Delta^{12}$-PGJ$_3$. The LSCs were isolated from mice treated with imatinib (75 mg/kg) for one week following which the treatment was stopped. The mice were followed for the development of leukemia. Mice that developed leukemia were euthanized and spleens were used as the source of LSCs.
Figure 9:
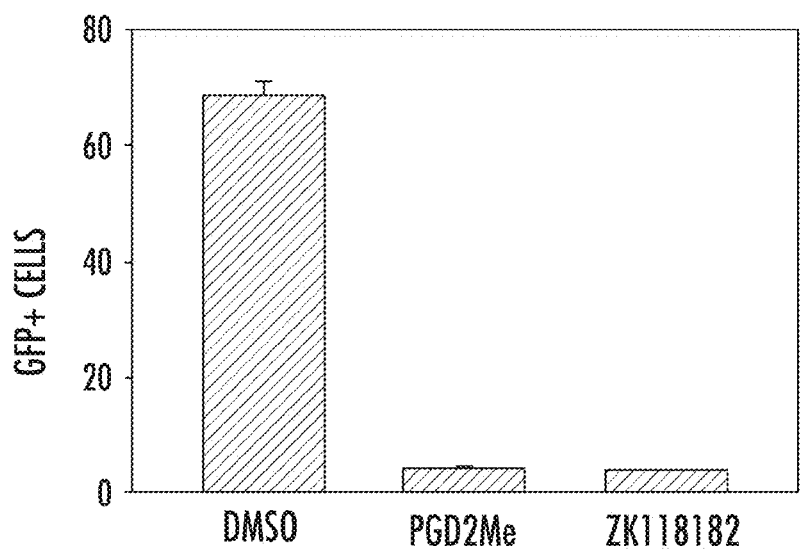
FIG. 9 is a graph showing apoptosis of BCR-ABL$^+$LSCs by synthetic agonists of the DPs.

The data shown in FIGS. 8 and 9 suggests a role of a class of G-protein coupled receptors (called DP), which play a role in the apoptosis of LSCs by $\Delta^{12}$-PGJ$_3$. In addition, experiments were performed with synthetic agonists of the receptor as well.

Referring to FIG. 8, this data shows that imatinib-resistant BCR-ABL(GFP)+ cells are targeted by $\Delta^{12}$-PGJ$_3$. In this experiment, mice were transplanted with BCR-ABL+LSCs and a week later imatinib treatment was initiated by i.p. for 1 wk at 25 mg/kg/day. After a 1 week washout period post imatinib treatment, spleens were dissected and the total splenocytes were treated ex-vivo with 25 nM $\Delta^{12}$-PGJ$_3$ or vehicle (PBS) for 24 h. GFP+LSCs were analyzed by flow cytometry. As shown in FIG. 8, $\Delta^{12}$-PGJ$_3$ treatment can even target LSCs that are resistant to imatinib treatment.

An experiment was performed that showed apoptosis of BCR-ABL+LSCs by $\Delta^{12}$ PGJ$_3$ is inhibited by synthetic antagonists of the DP. In this experiment, sorted BCR-ABL+ LSCs and MSCV-HSCs cultured in methocult media were pretreated with MK0824 (DP1 antagonist; 10 nM; Cayman Chem), CAY10471 (DP2 antagonist; 10 nM; Cayman Chem), or KU55933 (ATM kinase inhibitor; 10 nM; Calbiochem) for 2 h followed by 25 nM $\Delta^{12}$-PGJ$_3$ or DMSO. Following 36 h of incubation, apoptotic cells were quantified by annexin V staining. Viability of the MSCV-HSC control cells were not affected by any of the above treatments. Mean±s.e.m. of n=3. CAY10471 is an analog of Ramatroban (a approved human medication for the treatment of allergic rhinitis), which contains modifications that increase both its potency and selectivity for the human CRTH2/DP2 receptor. CAY 10471 binds to the human CRTH2/DP2, DP1, and TP receptors with Ki values of 0.6, 1200, and >10,000 nM, respectively. MSCV-HSCs (normal HSCs) were not affected by any of the treatments above. BCR-ABL LSCs on the other hand are highly susceptible to apoptosis by 25 nM $\Delta^{12}$-PGJ$_3$ and such an effect is inhibited by the use of DP antagonists. From this data, the pathway of apoptosis involves activation of DP and ATM kinase (Ataxia telangiesctasia mutated kinase protein). In a related study to address if $\Delta^{12}$-PGJ$_3$ treatment would cause any degranulation of granulocytes, a rat basophilic cell line (RBL-23) was treated with 100 nM $\Delta^{12}$-PGJ$_3$ and the degranulation was followed by quantitating the release of histamine and a second marker of degranulation, hexoseaminidase. Our results clearly indicate that $\Delta^{12}$-PGJ$_3$ did not cause degranulation, while ionomycin, a well-known stimulant of degranulation, caused extensive production of histamine and hexoseaminidase.

Referring to FIG. 9, this data shows apoptosis of BCR-ABL+ LSCs by synthetic agonists of the DP. In this experiment, 500,000 BCR-ABL+ LSCs were plated in a 24-well plate followed and were treated with 25 nM PGD2Me or 100 nM ZK118182 (both are agonists of DP) for 24 h. GFP+ cells were analyzed by flow cytometry. These agonists were purchased from Cayman Chemicals, MI. Based on this and the previous data, it is very clear that DP activation by synthetic agonists can induce apoptosis of LSCs. Thus, the use of synthetic compounds that are well-established DP agonists can target LSCs.

Example 3

Figure 10:
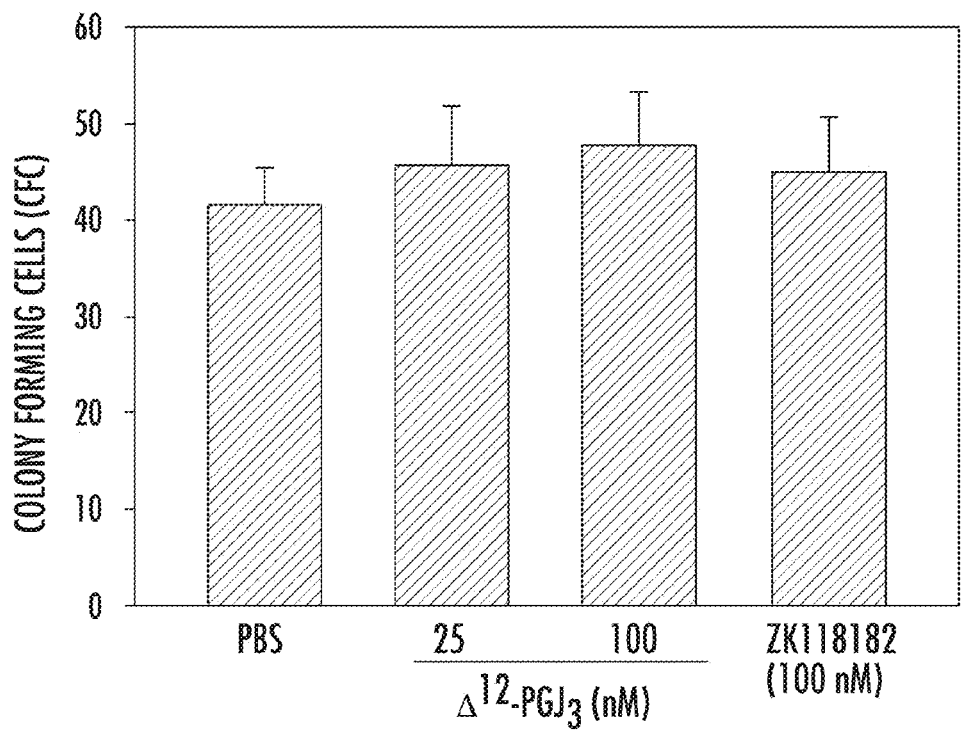
FIG. 10 is a graph showing that $\Delta^{12}$-PGJ$_3$ and related agonists do not affect normal human hematopoiesis as measured by the ability of bone marrow cells to form differentiated colonies when cultured in vitro. Human unfractionated bone marrow cells (5×10$^5$ per well) were plated in methylcellulose complete media containing IL-3, GM-CSF, G-CSF, SCF and Epo supplemented with the indicated concentrations of drugs. Total colonies were counted after 12 days.

$\Delta^{12}$-PGJ$_3$ and related agonists do not affect normal human hematopoiesis Referring to FIG. 10, this graph shows that $\Delta^{12}$-PGJ$_3$ and related agonists do not affect normal human hematopoiesis. In an experiment described above, the data showed the effects of $\Delta^{12}$-PGJ$_3$ on the formation of terminally differentiated hematopoietic cell colonies. These colonies are called colony forming cells or CFC. For that experiment, only growth factors necessary for multilineage myeloid colony formation were added. Referring to FIG. 10, media containing multiple growth factors supplemented with the compounds listed on the X axis of the graph was used. $\Delta^{12}$-PGJ$_3$ had no effect. The synthetic DP agonist ZK also had no effect. In conclusion, $\Delta^{12}$-PGJ$_3$ and related agonists do not affect normal human hematopoiesis.

Figure 11:
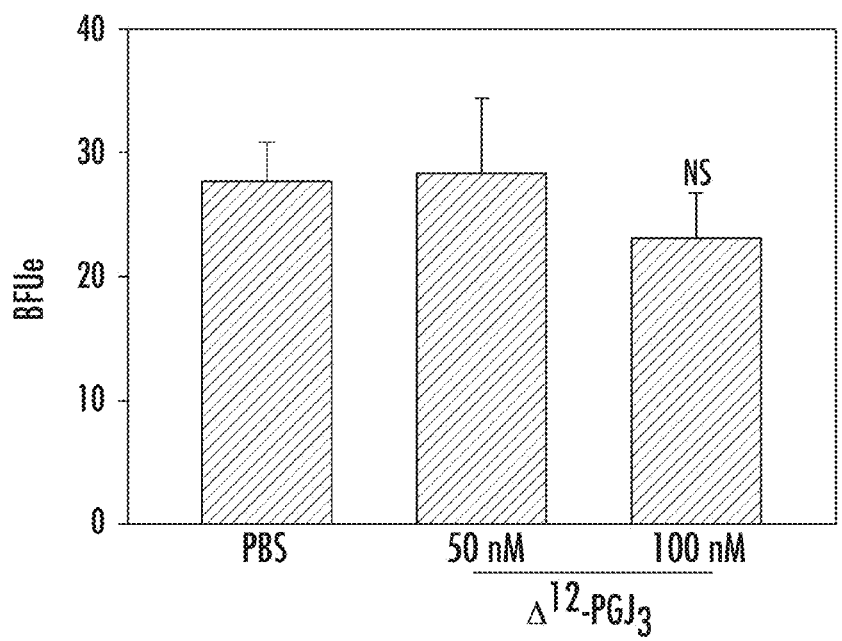
FIG. 11 is a graph showing that $\Delta^{12}$-PGJ$_3$ does not affect the ability of normal bone marrow cells to differentiate in to cells of the erythroid lineage (Burst Forming Units—erythroid, BFU-E).

Referring to FIG. 11, $\Delta^{12}$-PGJ$_3$ does not affect the ability of normal bone marrow cells to differentiate (to form BFUe). In this experiment, human bone marrow cells (CD34$^+$; Reach Bio, Seattle, Wash.) were cultured in Methylcellulose (Stem Cell Technology, H-4230) with Epo (3 U/ml)+SCF (50 ng/ml) for 8 days with PBS, $\Delta^{12}$-PGJ$_3$ (50 nM and 100 nM). BFUe colonies were stained with benzidine stain on day 8.

Example 4

Efficacy of $\Delta^{12}$-PGJ$_3$ and Comparative Data to Imatinib

An experiment involving a cytospin of Blast crisis CML (011711) and Geimsa stain was performed. Blast crisis CML were cultured in IMDM with BIT, LDL, L-Glu and treated with PBS or 100 nM $\Delta^{12}$-PGJ$_3$ for 12 hrs. Cells were collected and slides were done by Cytospin. Cytospin slides were stained with Wright Geimsa stain and pictures (100×) were recorded on a Material microscope. The studies confirm death of blast-crisis CML cells.

Figure 12:
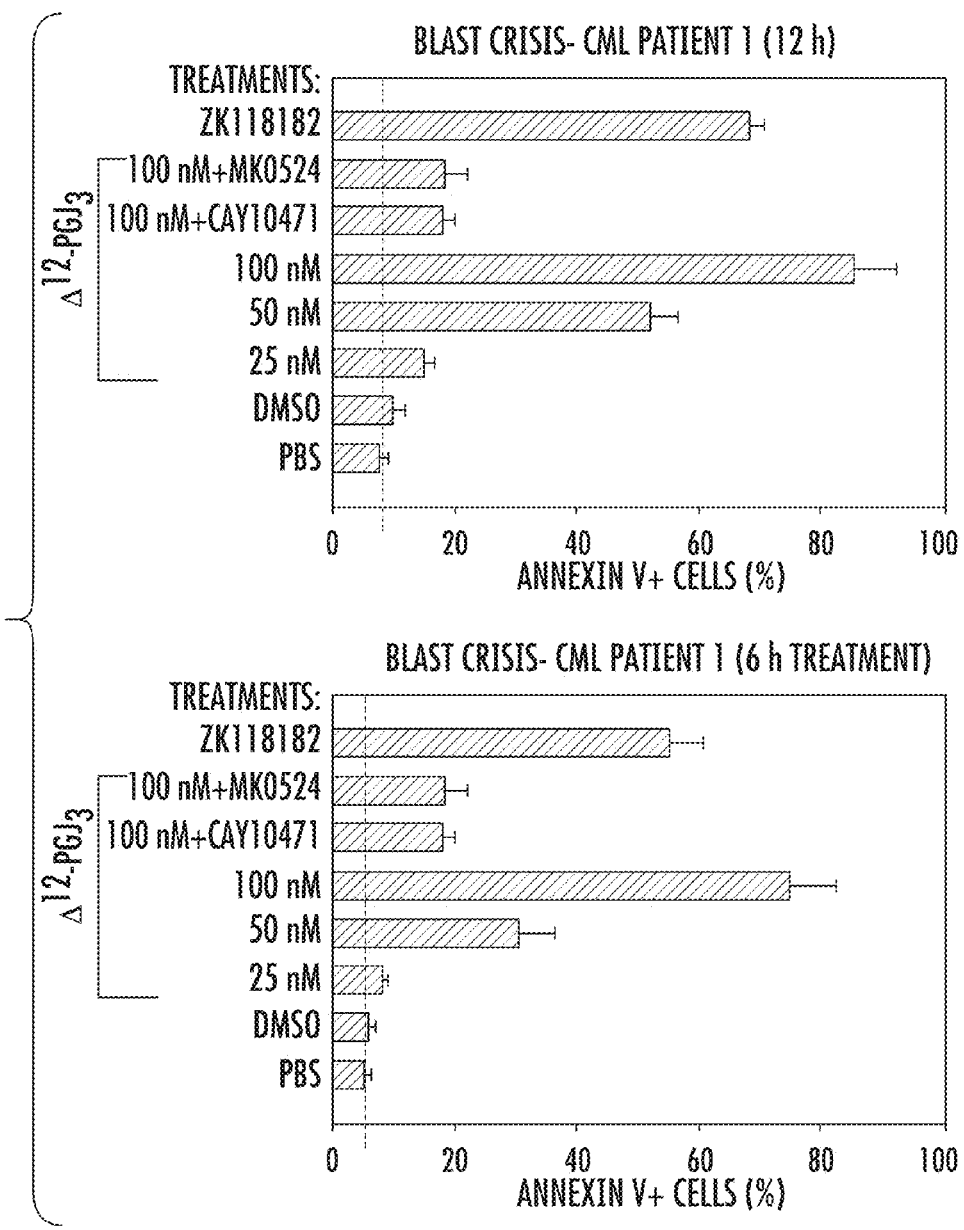
FIG. 12 is a pair of graphs showing that DP mediate the $\Delta^{12}$-PGJ$_3$-dependent apoptosis of blast crisis CML cells from a patient (#011711).
Figure 13A:
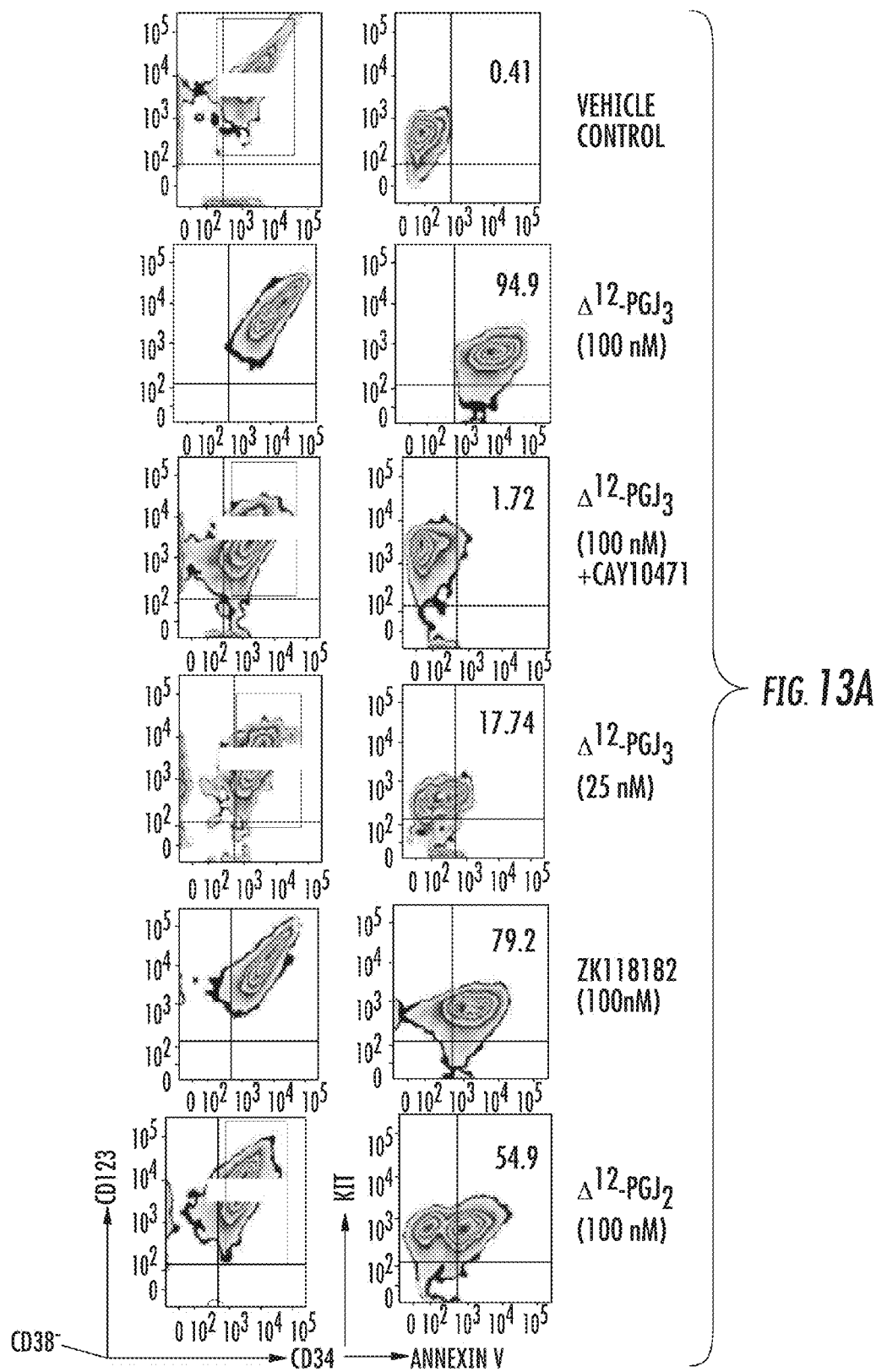
FIG. 13 shows results from an experiment in which DP mediate the $\Delta^{12}$-PGJ$_3$-dependent apoptosis of AML cells from a patient (#100810). Furthermore, $\Delta^{12}$-PGJ$_3$ also specifically targeted Leukemia stem cells (CD34+CD38-CD123+ cells) for apoptosis.
Figure 13B:
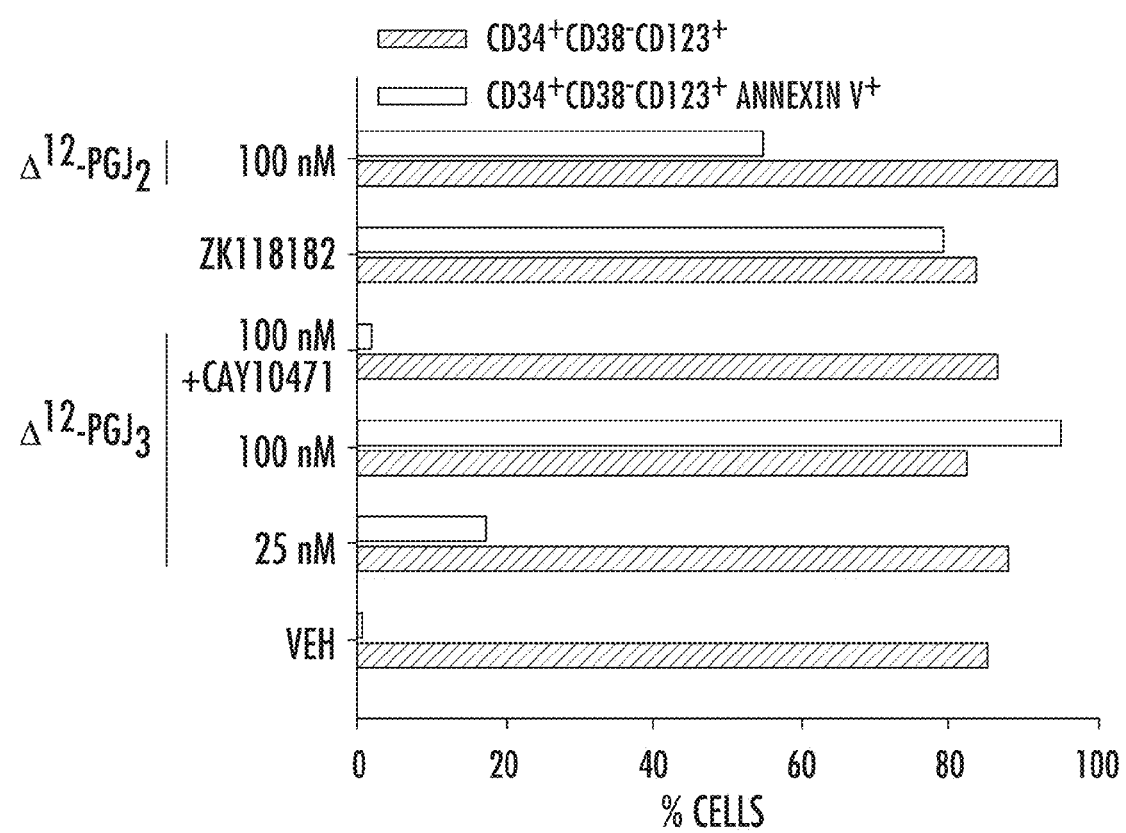

Referring to FIG. 12, the data in this pair of graphs shows that DP mediate the $^{\Delta 12}$-PG$_{J3}$-dependent apoptosis of blast crisis CML cells from a patient (#011711). In this experiment, 110,000/well primary AML cells were cultured in above specified media for 6 and 12 hrs. Cells were collected and washed once with ice cold PBS. The cells were resuspended in 200 ul 1× Apoptosis buffer with annexin-V PE to all tubes. The cells were washed in PBS and resuspended in 600 ul PBS and transfer into flow tubes and analyzed for apoptosis (Annexin V+ cells) on FC-500. The conclusion of this experiment is that $^{\Delta 12}$-PG$_{J3}$ or a synthetic DP agonist induces apoptosis in BC-CML primary patient cells. DP agonists block this response demonstrating that the effect of $^{\Delta 12}$-PG$_{J3}$ is DP dependent. Referring to FIG. 13, this figure shows that DP mediate the $^{\Delta 12}$-PGJ$_3$-PGJ$_3$-dependent dependent apoptosis of AML cells from a patient (#100810). In this experiment, 110,000/well AML cells were cultured in earlier mentioned media for 6 and 12 hrs. Cells were collected and washed once in PBS and resuspended in 200 ul PBS and blocked with FC receptor antibody 10 mins RT. The following antibodies were added: CD38, CD123, CD34, CD117 (BD bioscience) for 1 hr on ice. Cells were washed in PBS once and resuspended in 200 ul of apoptotic buffer, and annexin V was added and incubated for 15 mins. Apoptotic cells (Annexin V+ cells) were counted by flow cytometry. The conclusion from this experiment is that $^{\Delta 12}$-PGJ$_3$ induces apoptosis of primary human AML cells and that it can specifically kill LSCs as measured by analyzing the Annexin V+ fraction of the CD34+ CD38-CD123+CD117+ cells. Similar studies were performed with other AML patient samples (AML patient #123009, #033107, #041909, #101308) and the results (see FIG. 15) were identical to that described above. 4$^{12}$-PGJ$_3$ targeted the LSCs in all these samples. More importantly, pre-treatment of LSCs with CAY10471 (DP antagonist) completely blocked the apoptosis by 4$^{12}$-PGJ$_3$. Referring to the experimental results shown in FIG. 15, 110,000/well AML cells from patients #s 100810, 123009, 033107, 041909, 101308 were cultured in earlier mentioned media for 6 h with or without 100 nM $\Delta^{12}$-PGJ$_3$ (100 nM), or pretreatment with CAY10471 (10 nM) followed by D12-PGJ3 (100 nM). Cells were collected and washed once in PBS and resuspended in 200 ul PBS and blocked with FC receptor antibody 10 mins RT. The following antibodies were added: CD38, CD123, CD34 (BD bioscience) for 1 hr on ice. Cells were washed in PBS once and resuspended in 200 ul of apoptotic buffer, and annexin V was added and incubated for 15 mins. Apoptotic cells (Annexin V+ cells) were counted by flow cytometry. The conclusion from this experiment is that $\Delta^{12}$-$PGJ_3$ induces apoptosis of primary human AML cells and that it can specifically kill LSCs as measured by analyzing the Annexin V+ fraction of the CD34+CD38-CD123+ cells.

Survivin expression in the human AML sample post $\Delta^{12}$-$PGJ_3$ treatments was examined. Total RNA was isolated from AML cells with indicated treatments (for 6 h) using Trizol (Invitrogen) cDNA was generated using Superscript II (Invitrogen) and cDNA were quantified by RT-PCR using SYBR green PCR master mix and primers that amplify a 76 nt PCR product. A Taqman probe for GAPDH (Applied biosystems) was used. Survivin is an inhibitor apoptosis. $\Delta^{12}$-$PGJ_3$ decreases the expression of survivin suggesting that DP agonists suppress counter-regulatory pathways that inhibit apoptosis.

MCL-1 expression in $\Delta^{12}$-$PGJ_3$ treated AML was examined. MCL-1 is an antiapoptotic gene that belongs to the Bcl-2 family. Total RNA and cDNA were isolated from primary AML cells as indicated above. MCl-1 expression was measured using real time PCR. (Hs01050896-ml, Applied Biosystems). Treatment with $\Delta^{12}$-$PGJ_3$ decreases the expression MCL1 which is associated with increased apoptosis.

Figure 14:
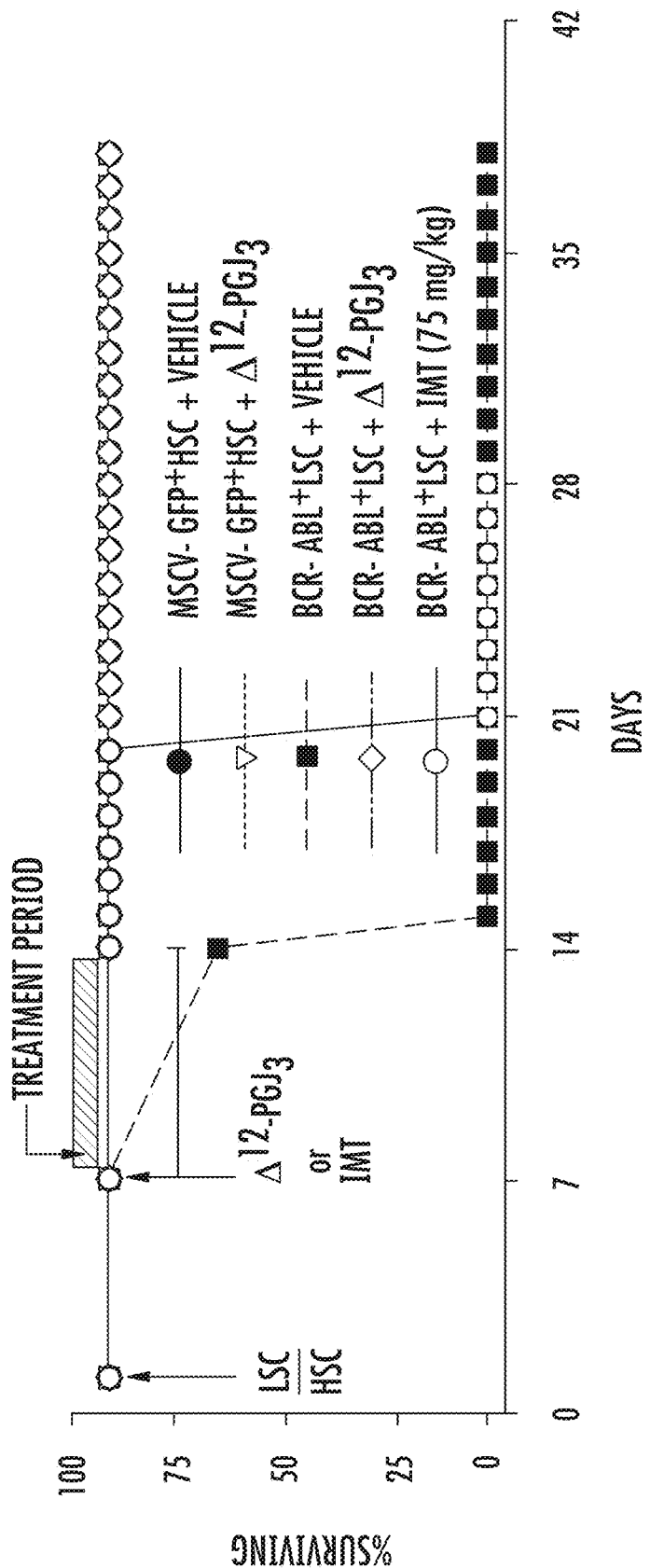
FIG. 14 is a graph showing results from a comparison of $\Delta^{12}$-PGJ$_3$ with Imatinib (Gleevec® Novartis, East Hanover, N.J.) in the BCR-ABL$^+$ LSC transplant CML model in mice.

Referring to FIG. 14, this graph shows a comparison of $\Delta^{12}$-$PG_{J3}$ with Imatinib (Gleevec) in the BCR-AB$^{L+}$LSC transplant CML model in mice. In this experiment, Imatinib and $\Delta^{12}$-$PG_{J3}$ were used at 75 mg/kg and 0.025 mg/kg, respectively. Treatment of a murine model for CML with the standard of care for CML patients, which is Imatinib therapy for 1 week leads to prolonged survival, but rapid relapse of leukemia. In contrast treatment with $\Delta^{12}$-$PG_{J3}$ leads to prolonged survival, but no relapse of leukemia.

Example 5

$\Delta^{12}$-$PGJ_3$ as an AML Chemotherapeutic

AML is one of the most common types of leukemia in adults. Unfortunately, the five year relative survival rates for AML are the lowest when compared to other forms of leukemia. AML is a stem cell disease where LSCs occupy the apex of the disease hierarchy. LSCs can self renew and generate non-stem cell progeny that make up the bulk of the leukemia cells. Although chemotherapy agents can effectively target bulk leukemia cells, LSCs have active mechanisms to avoid killing by these drugs. As a consequence, failure to eliminate LSCs results in relapse of the disease. Because of this property, specific targeting of LSCs is essential for successful treatment. Although the need for new anti-LSC based therapies is well recognized, the identification of mechanism-based drugs to target LSCs has been lacking. Clearly new approaches are needed. A metabolite derived from ω-3 fatty acids, $\Delta^{12}$-$PGJ_3$, was discovered which effectively eradicates LSCs in two mouse models of chronic leukemia. In the experiments described herein, these findings were extended to show that $\Delta^{12}$-$PGJ_3$ effectively targets AML LSCs by inducing apoptosis in murine models of AML and in human AML leukemia samples. In contrast, $\Delta^{12}$-$PGJ_3$ has no effect on normal hematopoietic stem cells or the differentiation of hematopoietic progenitors. $\Delta^{12}$-$PGJ_3$ acts by inducing the expression of p53 in LSCs and leukemia cells. High-level expression of p53 in LSCs is incompatible with self renewal and leads to apoptosis. These data suggest that $\Delta^{12}$-$PGJ_3$ is a chemotherapeutic agent for treating AML.

Example 6

Figure 16:
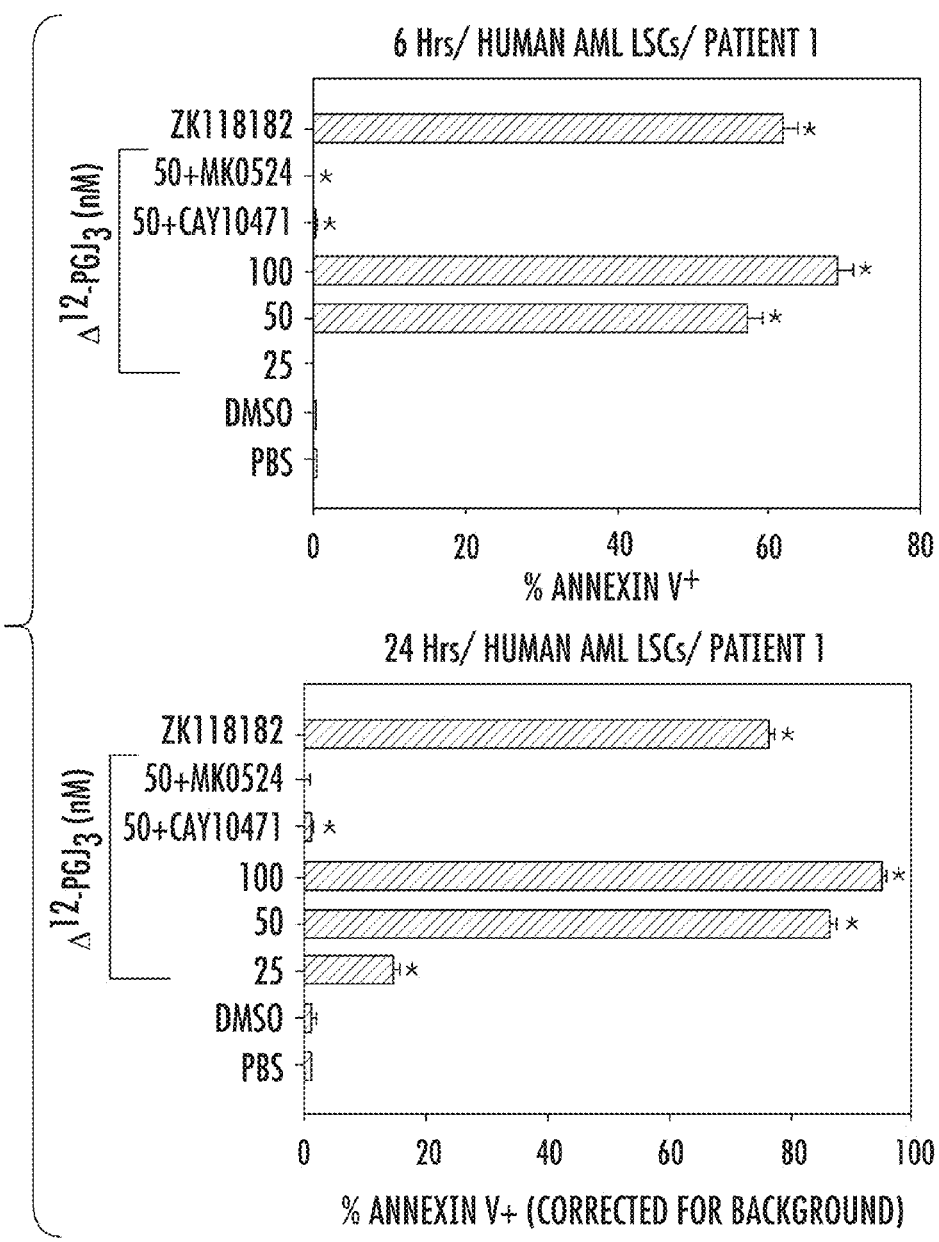
FIG. 16 is a pair of graphs showing apoptosis of human primary AML cells by DP agonists (endogenous and exogenous) and DP antagonists.

Apoptosis of Human Primary AML Cells by DP Agonists (Endogenous and Exogenous) and DP Antagonists Referring to the results shown in FIG. 16, these experiments were performed with primary AML stem cells isolated from a patient. These results strongly support the fact that $\Delta^{12}$-$PGJ_3$ (and other DP agonists) are effective even in human primary leukemia stem cells even from an AML patient. Human primary AML cells isolated from the bone marrow of an AML patient (72% of the cells were CD133+) were treated in-vitro with various concentrations of $\Delta^{12}$-$PGJ_3$ (5, 50, 100 nM) in the presence or absence of DP antagonists (CAY10471 and MK0524, both 10 nM) for 6 and 24 h. In an identical experiment, the cells were also treated with a synthetic DP agonist, ZK118182 (100 nM). Apoptosis of cells (by annexin V staining) was measured using flow cytometry. These results are in agreement with the data described above with mouse AML stem cells, which further supports the use of DP agonists as a therapy for leukemias.

Other Embodiments

Any improvement may be made in part or all of the compositions, kits, and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A composition comprising a pharmaceutically acceptable carrier and a therapeutically effective amount of a first anti-cancer drug consisting of: isolated or synthesized $D^{12}$-prostaglandin $J_3$ ($D^{12}$-$PGJ_3$) for inhibiting leukemia stem cell (LSC) growth in a subject having LSCs.

2. The composition of claim 1, further comprising a second anti-cancer drug.

3. The composition of claim 2, wherein the second anti-cancer drug is imatinib.

4. A method of treating leukemia in a subject, comprising administering to the subject having leukemia a composition comprising a pharmaceutically acceptable carrier and at least a first anti-cancer drug consisting of: isolated or synthesized $D^{12}$-prostaglandin $J_3$ in a therapeutically effective amount for inhibiting LSC growth in a subject having LSCs.

5. The method of claim 4, wherein the LSCs are chronic myeloid leukemia stem cells or acute myeloid leukemia cells.

6. The method of claim 4, wherein the subject is resistant to imatinib.

7. The method of claim 4, wherein the subject is a human.

8. The method of claim 4, wherein the composition further comprises a therapeutically effective amount of a second anti-cancer drug.

9. The method of claim 8, wherein the second anti-cancer drug is imatinib.

10. The method of claim 4, wherein administration of the composition induces apoptosis of the LSCs in the subject.

11. The method of claim 4, wherein administration of the composition eliminates LSCs in the subject.

12. A kit for treating leukemia in a subject, the kit comprising:
   (a) a composition comprising a pharmaceutically acceptable carrier and at least a first anti-cancer drug consisting of: isolated or synthesized $D^{12}$-prostaglandin $J_3$ in a therapeutically effective amount for inducing death of LSCs in the subject;
   (b) instructions for use; and
   (c) packaging.

13. The kit of claim 12, wherein the kit further comprises a therapeutically effective amount of a second anti-cancer drug.

14. The kit of claim 13, wherein the second anti-cancer drug is imatinib.

* * * * *